United States Patent [19]
Cornell et al.

[11] Patent Number: 5,874,316
[45] Date of Patent: *Feb. 23, 1999

[54] RECEPTOR MEMBRANES AND IONOPHORE GATING

[75] Inventors: Bruce A. Cornell; Vijoleta L. B. Braach-Maksvytis, both of New South Wales; Ronald J. Pace, Australian Capital Territory; Lionel G. King, New South Wales; Burkhard Raguse, New South Wales; Peter D. J. Osman, New South Wales, all of Australia

[73] Assignee: Australian Membrane Biotechnology Research Institute, New South Wales, Australia

[*] Notice: The term of this patent shall not extend beyond the expiration date of Pat. Nos. 5,436,170 and 5,443,955.

[21] Appl. No.: 741,299

[22] Filed: Oct. 30, 1996

Related U.S. Application Data

[63] Continuation of Ser. No. 449,962, May 25, 1995, abandoned, which is a continuation-in-part of Ser. No. 721,431, Jul. 3, 1991, Pat. No. 5,443,955.

[30] Foreign Application Priority Data

| Jan. 27, 1989 | [AU] | Australia | PJ2441 |
| Jan. 30, 1989 | [AU] | Australia | PJ2469 |
| Jan. 30, 1989 | [AU] | Australia | PJ2470 |
| Jan. 29, 1990 | [WO] | WIPO | WO90/00025 |

[51] Int. Cl.$^6$ ............... G01N 33/543; G01N 33/566; G01N 33/53; C12N 1/00
[52] U.S. Cl. ............ 436/518; 435/7.1; 435/817; 435/317.1; 436/501; 436/512; 436/524; 436/525
[58] Field of Search ............ 435/7.1, 7.2, 7.21, 435/317.1; 436/501, 512, 518, 524, 525, 532, 547, 806, 829

[56] References Cited

U.S. PATENT DOCUMENTS

| 4,342,826 | 8/1982 | Cole . |
| 4,517,303 | 5/1985 | Freytag et al. . |
| 4,661,235 | 4/1987 | Krull et al. . |
| 4,758,342 | 7/1988 | Heckmann et al. . |

FOREIGN PATENT DOCUMENTS

| 40123/85 | 10/1985 | Australia . |
| B-50889/85 | 11/1989 | Australia . |
| 0 261 887 | 3/1988 | European Pat. Off. . |
| WO85/05548 | 12/1985 | WIPO . |
| WO89/01159 | 2/1989 | WIPO . |

OTHER PUBLICATIONS

Krull et al "Lipid membrane technology for chemical . . . " Trends in Analytical Chemistry, vol 4, 1985, pp. 90–96.
Huang et al. "Interactions of Immunoliposomes . . . " The Journal of Biological Chemistry, 254(22): 14034–14040.
D. E. Williams "Electrochemical noise and chemical sensing" Biosensor Technology, Conf. 11, Sep. 11, 1987, pp. 203–208.
Young et al "Mouse macrophage Fe receptor . . . " Proc. Natl Aca. Sci., vol 80 Mar. 1983, pp. 1636–1640.
Corcia et al "Characterization of ion channel . . . " The EMBO Jour., vol 5 No. 5, pp. 849–854.
G.M. Sankolli et al "Improvement in the antibody binding . . . " Journal of Immunology methods, 104(1987), pp. 191–194.

*Primary Examiner*—James C. Housel
*Assistant Examiner*—Rodney P. Swartz
*Attorney, Agent, or Firm*—Nixon & Vanderhye

[57] ABSTRACT

The present invention provides a membrane the conductivity of which is dependent on the presence or absence of an analyte. The membrane comprises a closely packed array of self-assembling amphiphilic molecules and two ionophore components. A receptor molecule reactive with the analyte is provided on one of the ionophore components. The binding of the analyte to the receptor molecule causes a change in the relationship between the ionophore components such that the flow of ion across the membrane is prevented or allowed. The ionophore components are preferably selected from the group consisting of amphotericin B, gramicidin A monomers and combinations thereof, with gramicidin A monomers being particularly preferred. The present invention also provides a membrane including receptors directed against the Fc region of antibodies. These receptors are preferably derived from polyclonal antibodies. These membranes provide a "generic" surface which will bind antibodies in a manner such that the antigen binding regions of the antibody are not hindered. The present invention further provides a device adapted for implantation in a mammalian body, the device being characterized in that it is coated with a membrane comprising a closely packed array of self-assembling amphiphilic molecules and receptor molecule. The receptor molecules being such that the attachment of specific cells to the membrane is enhanced or avoided. It is particularly preferred that the receptor molecules are directed against fibronectin, vitronectin, endothelial cells, or epithelial cells. It is further preferred that the membrane coating the device also includes a plurality of ion channels such as gramicidin.

33 Claims, 16 Drawing Sheets

RECEPTOR MEMBRANES AND IONOPHORE GATING

This is a Continuation of application Ser. No. 08/449,962, filed 25 May 1995, now abandoned, which is a continuation in part of Ser. No. 07/721,431, filed Jul. 3, 1991 now U.S. Pat. No. 5,443,950.

The present invention relates to a membrane bilayer in which each layer has incorporated therein ionophores and in which the conductance of the membrane is dependant on the presence or absence of an analyte. The present invention further relates to membranes including receptors directed against the Fc region of antibodies. In addition, the present invention also relates to devices adapted for implantation in a mammalian body, the surface of the device being coated with a membrane which includes receptors.

It is known that amphiphilic molecules may be caused to aggregate in solution to form two dimensional membrane arrays in a variety of morphologies such as monolayers, black lipid membranes, vesicles and liposomes. It is also known that such amphiphilic molecules may be formed with cross linkable moieties. Under appropriate stimulus, such as UV radiation or ionizing radiation, the cross-linkable moieties can be caused to polymerize after the amphiphilic molecules have been caused to assume a suitable ordered two dimensional array. It is also known that suitable receptor molecules may be included in ordered arrays of amphiphilic molecules.

The selectivity and flux of ions through membranes can depend on the number, size and detailed chemistry of the pores or channels they possess. It is through these pores or channels that the permeating solubilized molecules pass across the membrane, It is also known that membranes may incorporate a class of molecules, called ionophores which facilitate the transport of ions across these membranes.

In co-pending application No. WO 89/01159 it is disclosed that suitably modified receptor molecules may be caused to co-disperse with amphiphilic molecules and produce membranes with altered surface binding properties, which are useful in the production of biosensor receptor surfaces of high binding ability and high binding specificity. It is also disclosed in this co-pending application that ion channels such as polypeptide ionophores may be co-dispersed with amphiphilic molecules, thereby forming membranes with altered properties in relation to the permeability of ions. This application also discloses various methods of gating these ion channels such that in response to the binding of an analyte the conductivity of the membrane is altered. The disclosure of application No. WO 89/01159 is incorporated herein by way of reference.

When membranes formed from these various components are maintained at a temperature above a critical temperature, Tc, variously known as the transition temperature, chain melting temperature or phase transition temperature, the ion channels, and receptor molecules present in the membrane are able to diffuse laterally within the two dimensional plane of the membrane.

Immunoglobins possess characteristics such as high specificity, high affinity, variety and stability, which make them ideal for use as analytical reagents. Antigen-antibody interactions form the basis of sensitive diagnostic techniques such as radioimmunoassay (RIA) and enzyme-linked immunosorbant assay (ELISA). Although these techniques are sensitive and widely used, commercial antibody-based diagnostic kits which include disposable single-use devices are semi-quantitative, time-consuming and cannot be calibrated which limits their analytical potential. The optimum immuno-based assay system should be fast, reliable, specific, sensitive and quantitative.

ELISA's and RIA's commonly immobilize the antibody via non-covalent association of antibodies with glass or plastic surfaces. This typically blocks many antibody binding sites, reducing activity and preventing precise quantitation of the number and affinity of the remaining sites. More recently, orientation of antibody binding sites has been achieved by specific attachment of the antibody or antibody fragments, $F(ab)_2$ and Fab, to a surface via groups remote from the antigen binding region. The binding between the antibody and antigen can be detected by a variety of methods some of which use electrical measurements. However, this procedure requires that for each new analyte to be detected, the specific antibody raised against the analyte must be affinity purified from a polyclonal mixture so that further reduction to the $F(ab)_2$ or Fab fragments can be carried out.

The present invention involves the orientation of the antigen-binding portion of the chosen monoclonal or polyclonal antibody such that the antigen-binding site remains free and unhindered. The monoclonal status is not a prerequisite for the antigen detection technique, and further reduction to $F(ab)_2$ or Fab fragments is not required. The antibody raised against the analyte to be detected (A) is bound to acylated antibody or antibody fragments (B) incorporated into a self-assembled monolayer or bilayer membrane composed of amphiphilic molecules.

It is also believed that membranes including receptor molecules may be used to coat devices for implantation, and that such coating would render the surface biocompatible.

Biocompatible surfaces are needed for any invasive prosthetic device. Depending on the type of device and the location within the body, the prosthetic device needs to have a surface which will encourage the adhesion of certain cells while repelling other types of cells, For example, adsorption of plasma proteins such as fibrinogen or attachment of cells such as erythrocytes can lead to thrombosis, and adsorption of cells to surfaces which lead to tissue build-up, are both undesirable consequences of interfacing tissue with a foreign surface. However, at the point of entry of an invasive prosthetic device into the body, cell-surface adhesion can act as a seal against the spread of bacteria and hence infection along the device and into the body.

A strategy to promote the beneficial adhesion between the surface of the invasive device and desired cells, whilst at the same time preventing the attachment of undesirable cells and plasma proteins, is to encourage the adhesion to the surface of the invasive device of specific cells such as epithelial or endothelial cells via their cell surface attachment proteins such as fibronectin and vitronectin.

In a first aspect the present invention consists in a membrane in which the conductance of the membrane is dependent on the presence or absence of an analyte, the membrane comprising a closely packed array of amphiphilic molecules and a plurality of ionophores comprising a first and second half membrane spanning monomer, at least the second half membrane spanning monomer being capable of lateral diffusion within the membrane, a first receptor molecule provided on at least the second half membrane spanning monomers, said first receptor molecule being reactive with the analyte or a portion thereof, the binding of the analyte to the first receptor molecule causing a change in the relationship between the first half membrane spanning monomer and the second half membrane spanning monomer such that the flow of ions across the membrane via the ionophores is allowed or prevented.

In a preferred embodiment of the present invention the membrane comprises a first and a second layer, the first half membrane spanning monomers being provided in the first layer and the second half membrane spanning monomers being provided in the second layer.

The half membrane spanning monomer can be any of such molecules known in the art, however, it is presently preferred that the monomers are selected from the group consisting of gramicidin A monomers, amphotericin B, and combinations thereof. It is most preferable that the monomers are gramicidin A monomers.

In a preferred embodiment of a first aspect of the present invention the first half membrane spanning monomers in the first layer are prevented from lateral diffusion within said first layer and the second half membrane spanning monomers in the second layer are capable of lateral diffusion within said second layer.

The first half membrane spanning monomer in the first layer may be prevented from diffusing laterally using any of a number of known techniques, however, it is presently preferred that the monomer and the amphiphilic molecules each include or are decorated with at least one moiety cross-linked with at least one corresponding moiety on another of these molecules. Under appropriate stimulus, such as UV radiation or ionizing radiation, the cross-linkable moieties can be caused to polymerize thereby resulting in the membrane being cross-linked in one layer.

The first half membrane spanning monomers may also be prevented from diffusing laterally by selecting lipids for the first layer of the membrane which are crystalline at room temperature. This eliminates lateral diffusion in the first layer.

In a further preferred embodiment of the present invention the first half membrane spanning monomer in the first layer is prevented from diffusing laterally by fixing the first layer and the monomers therein to a solid support. This may be achieved by providing groups on the amphiphilic molecules in the first layer and on the monomers therein which are reactive with the solid support or with corresponding groups provided thereon.

In a further preferred embodiment of this aspect of the present invention the membrane includes a plurality of second receptor molecules having receptor sites. It is also preferred that the second receptor molecules are prevented from diffusing laterally within the membrane.

In the situation where the membrane is a bilayer it is preferred that the second receptor molecule is provided in the second layer such that Its receptor sites project outwardly from the surface of the second layer remote from the first layer.

As used herein the term "receptor molecule" is used in its widest context. The receptor molecule may be any chemical entity capable of binding to the desired analyte. The receptor molecule is any compound or composition capable of recognize another molecule. Natural receptors include antibodies, enzymes, lectins, dyes, chelating agents and the like. For example the receptor for an antigen is an antibody, while the receptor for an antibody is either an anti-antibody or, preferably, the antigen recognised by that particular antibody. In addition, the receptor for an ion such as calcium would be the chelating agent EDTA.

The first and second receptor molecules may be the same or different and are preferably selected from the group consisting of polyclonal or monoclonal antibodies, fragments thereof including at least one Fab fragment, antigens, lectins, haptens, chelating agents and dyes and are most preferably antibodies or fragments thereof.

It is also preferred that first receptor molecule, and optionally the second receptor molecule, has two receptor sites for the analyte.

The second receptor molecule is preferably an antibody or fragment thereof including at least one Fab fragment or antibody. When the receptor molecule is an Fab fragment or antigen this may be conjugated with a supporting entity such as is described in application WO 89/01159. The second receptor molecule may be prevented from diffusing laterally within the second layer by any of a number of known means such as cross-linking of the receptor molecule to amphiphilic molecules within the second layer. In the situation where the receptor molecule is conjugated with a supporting entity it is possible to prevent lateral diffusion of the receptor moiety by having the supporting entity extend through both the second and first layers.

When the membrane of the present invention is used in a biosensor it is preferred that the membrane is attached to a solid surface. This may be achieved by providing groups reactive with the solid surface on the amphiphilic molecules in the membrane. Preferred solid surfaces include hydrogel, ceramics, oxides, silicon, polymers and transition metals. Preferred transition metals are gold, platinum and palladium. The attachment of the membrane to a solid surface may be achieved by non-covalent attraction or by covalent reactions. For example, vinyl groups on a solid substrate could be copolymerized with a vinyl-terminated lipid; a sulphur-terminated lipid could be adhered to a metal (e.g. gold or palladium) substrate; or condensation or addition reactions could be used to anchor the lipid. Modification of the solid substrate, if necessary, can be achieved using any of the known techniques such as silylation or silica surfaces. In the situation where the membrane is a bilayer, the first layer is attached to the solid surface.

Preferably the second layer is selected to have a phase transition temperature such that cooling of the membrane below this temperature induces phase separation in the second layer thereby releasing any analyte bound to either the first and/or second receptor molecules. This should provide a convenient method of "resetting" the device following a test.

In preferred embodiments of this aspect of the present invention the first receptor is attached to the ionophore via a linker group. This linker group typically comprises a spacer group and one or more reactive groups, the spacer group being attached to ionophore and the reactive group providing attachment to the receptor molecule. The spacer group can consist of hydrocarbons, oligomers of ethylene glycol, oligo-peptides etc. and is of a length such that the ionophore is able to conduct ions when the receptor molecule is coupled. The reactive groups can consist of N-hydroxysuccinimide esters or other common activated esters for covalent coupling to amine groups on proteins, hydrazine derivatives for coupling onto oxidized sugar residues; maleiimide derivatives for covalent attachment to thiol groups; biotin; streptavidin or antibodies.

The linker group may consist of a number of reactive groups, for example, in one preferred embodiment of the present invention the linker group comprises a spacer group which is attached to biotin which in turn is attached to streptavidin. With this particular linker group the receptor molecule to be bound would be a biotinylated antibody, the biotin on the antibody binding to the streptavidin.

In a further preferred embodiment of the present invention the terminal reactive group on the linker is an antibody or antibody fragment directed against the Fc portion of an antibody. With such a terminal reactive group the linker will bind to the Fc region of an antibody which will be the receptor molecule directed against the analyte.

In a further preferred embodiment of the present invention the second receptor molecule is attached to the membrane using similar linker groups.

In a preferred embodiment of the present invention the first receptor molecules on separate second half membrane spanning monomers bind to different sites on the analyte, such that binding of the first receptors to the analyte results in the prevention of the flow of ions across the membrane.

In a further preferred embodiment of the present invention the first receptor molecules on separate second half membrane spanning monomers are bound to different sites on the analyte or an analog thereof, such that the flow of ions across the membrane is prevented, the addition of analyte effecting competitive binding with the first receptor molecules resulting in the flow of ions across the membrane.

In yet a further preferred embodiment of the present invention at least a proportion of the amphiphilic molecules are membrane spanning amphiphiles, the membrane spanning amphiphiles being archeobacterial lipids or tail to tail chemically linked bilayer amphiphiles. In the embodiment where the membrane exists as a mono-layer, it is preferred that all the amphiphilic molecules are membrane spanning amphiphiles.

As is stated above one of the preferred terminal reactive groups on the linker molecule is streptavidin. This would typically be bound to the spacer group by way of a biotin reactive group. When using such a multivalent reactive group it is essential that the linker groups are not able to cross-link as this would result in a change in the relationship between the ionophores in the first layer and the ionophores in the second layer in the absence of any analyte. Accordingly, when a molecule such as streptavidin is to be used as the terminal reactive group it is essential that the ability of the streptavidin to cross-link with the biotin provided on other linker groups is prevented. This may be done by ensuring that the biotin binding site of the streptavidin adjacent to the biotin binding site by which the streptavidin is bound to the linker group is occupied by biotin. This can be achieved by pre-incubating the streptavidin with an appropriate amount of biotin.

In the absence of competing influences the ionophores in each of the first and second layers will, on average, align themselves to produce an intact channel which allows the passage of ions through the membrane. When the ionophores in the second layer diffuse out of alignment with the ionophores in the first layer, the channel will be broken and ions will not pass through the membrane. With this arrangement the diffusion of the ionophores may, when incorporated into a suitable membrane, be used to detect as little as a single molecule of analyte. The attachment of a single molecule of analyte may cause an intact ion channel to be formed or broken either allowing or stopping the flow of ions across the membrane. After a brief time this change in passage of ions across the membrane may be detected as the signal for the binding of the analyte to a receptor. The measurement of current flow across membranes due to a single ionophore is known and typically yields a current of 4 pA per channel.

In a second aspect the present invention consists in a membrane in which the conductance of the membrane is dependent on the presence or absence of an analyte, the membrane comprising a closely packed array of amphiphilic molecules and a plurality of membrane spanning helical peptide aggregate ionophores comprising a plurality of membrane spanning helical peptide monomers each provided with a receptor molecule reactive with the analyte, binding of the analyte to the receptor molecule causing disruption of the membrane spanning helical peptide aggregate.

In a preferred embodiment of this aspect of the present invention the membrane spanning helical peptide monomers are alamethicin monomers.

In a further preferred embodiment of this aspect of the present invention the receptor molecules are selected from the group consisting of polyclonal or monoclonal antibodies, antibody fragments including at least one Fab fragment, antigens, lectins, haptens, chelating agents and dyes. However, at present it is preferred that the receptor molecules are antibody fragments including at least one Fab fragment and preferably an Fab fragment.

The membrane may exist as either as a bilayer or monolayer and in the situation where the membrane is a monolayer, it is preferred that the amphiphilic molecules are membrane spanning amphiphiles such as archeobacterial lipids or tail to tail chemically linked bilayer amphiphiles.

When the membrane of this aspect of the present invention is used as a biosensor it is preferred that the membrane is attached to a solid surface. This may be achieved by providing groups reactive with the solid surface on the amphiphilic molecules in the membrane. Preferred solid surfaces include hydrogel, ceramics, oxides, silicon, polymers and transition metals. Preferred transition metals are gold, platinum and palladium. The attachment of the membrane to a solid surface may be achieved by non-covalent traction or by covalent reactions.

In further preferred embodiments of this aspect of the present invention the receptor molecules are attached to the membrane spanning helical peptide monomers via a linker group. This linker group is as previously described in the first aspect of the present invention.

As is known, alamethicin ionophores consist of aggregates of alamethicin monomers which associate to form conducting ionophores. It is believed that the aggregation/association of alamethicin monomers in a membrane would be prevented if these monomers are provided with a receptor group which is subsequently bound to an analyte.

In a third aspect the present invention consists in a membrane for use in detecting the presence of an analyte, the membrane comprising a closely packed array of self-assembling amphiphilic molecules wherein at least a proportion of the self-assembling amphiphilic molecules comprise a receptor molecule conjugated with a supporting entity, the receptor molecule having a receptor site and being reactive with the Fc region of an antibody, the receptor molecule being selected from the group consisting of the Fc binding domain of an Fc receptor, an antibody, $F(ab)_2$ and Fab fragments; the supporting entity being selected from the group consisting of a lipid head group, a hydrocarbon chain(s), a cross-linkable molecule and a membrane protein; the supporting entity being conjugated with the receptor molecule at an end remote from the receptor site, and in which antibody molecules reactive with the analyte are bound to the receptor molecule by their Fc region.

As used herein the term "Fc receptor" is defined as cell membrane receptors reactive against the Fc portion of immunoglobulin.

In a preferred embodiment of this aspect of the present invention the receptor molecules are preferably derived from polyclonal antibodies. It is also presently preferred that the receptor molecules are covalently attached to the supporting entity via their amino acid side chains or carbohydrate moieties.

In a further preferred embodiment of the present invention, the receptor molecules conjugated to the supporting entity are able to diffuse laterally through the membrane bilayer or monolayer.

In a further preferred embodiment of the present invention, the antibody reactive with the analyte is a monoclonal antibody. It is also presently preferred that the antibody reactive with the analyte may consist of two or more different monoclonal antibodies directed against different epitopes present on the same analyte.

As would be readily appreciated by a person skilled in the art, by using receptor molecules directed against the Fc portion of species-specific antibodies, for example anti-mouse Fc antibodies or $F(ab)_2$ of Fab fragments thereof, the membrane of the present invention can be used with any mouse antibody.

The membrane of the present invention is generally first prepared from antibodies raised against the Fc portion of species-specific antibodies, eg. anti-mouse Fc antibodies. In the situation where antibody fragments are used these anti Fc antibody fragments (B) are preferably covalently attached to the supporting entity via their terminal amino acid side chain or carbohydrate moieties and incorporated into the self-assembled amphiphilic monolayer or bilayer. The antibody (A) raised against the desired analyte to be detected may be of monoclonal or polyclonal nature. The antibody (A) is then bound to the self-assembled monolayer or bilayer via its Fc region by the anti Fc antibody fragments (B) which are incorporated into the monolayer or bilayer.

Where the receptor molecule is the Fc binding domain of an Fc receptor, it is preferred that the Fc receptor is selected from the class of receptors known as Fc δ RI or Fc δ RII or Fc δ RIII. It is particularly preferred that the Fc receptor is reactive against the Fc portion of IgG.

As stated above only the Fc binding domain of the Fc receptor is used, optionally together with the transmembrane domain. Whilst this portion could be generated by isolating the whole receptor molecule, it is believed to be preferable to produce the extracellular Fc binding domain or the extracellular Fc binding domain together with the transmembrane domain using genetic engineering techniques. To achieve this cloned genes encoding the Fc receptor would be modified to produce only the relevant domain(s). This will, of course, involve deletion of a portion of the gene sequence.

It is also envisaged that further modifications of the gene sequence may be made for both Fc receptors and antibodies. These include, for example, for the extracellular domain of the Fc receptor, or the antibodies addition of one or more amino acids including a cysteine residue to provide a sulphydryl group which may be required for chemical cross-linking of the Fc receptor or antibody binding domain to the membrane molecules. This would be achieved by site directed mutagenesis.

It is also envisaged that modifications may be made to the gene sequence encoding the Fc binding domain to increase the affinity of the receptor for bound antibody and/or to increase the range of IgG molecules bound by Fc δ RI, Fc δ RII and/or Fc δ RIII. Modifications may also be made to the gone sequence of the antibody binding domain to increase binding affinity.

The lipid matrix of the membrane ensures the incorporation of the antibody and the correct orientation of each antibody molecule. This self-assembled monolayer or bilayer may be formed by any of the known methods such as the Langmuir-Blodgett technique, liposomes or BLM.

Preferably detection of antigen-binding interactions is carried out using transduction measurements. It is preferred that the membrane of the present invention is attached to a solid support such as a metal, polymer or hydrogel. The detection mechanism may be achieved by choosing a conducting solid support which can detect the antigen-antibody binding event. The detection of the binding event will depend on the preferred phase separation of the antibody-antigen complexes from the amphiphilic molecules in the membrane on the surface of the conducting solid support, thus bare conducting solid support is exposed to an aqueous environment thereby changing the transduction measurement. The phase separation of the antibody attached to freely diffusing antibody fragments incorporated into the membrane depends on the binding of the desired antigen by at least two different antibodies raised against the same analyte. The binding of two or more antibodies induces clustering of the antibodies which alters the phase of the monolayer or bilayer rendering it "leaky" to the aqueous environment. This "leakiness" changes the transduction property of the conducting solid support which is no longer insulated from the aqueous environment by the membrane.

The density of antibodies present in the membrane can be varied by varying the ratio of amphiphile to antibody-supporting entity conjugate. Increased stability of the membrane of the present invention may be achieved by placing the membrane on a solid support. Appropriate treatment of the chosen solid support enables covalent linkage of the hydrocarbon chains of the amphiphile and supporting entity to the solid support. The choice of amphiphile used in the membrane may be such that, upon binding of the antigen, the monolayer or bilayer phase of the solid support is disrupted rendering the surface "leaky", as is known in the art. Such a device can be designed to have an "all or nothing" response to a chosen minimum quantity of antigen present in the testing solution.

In summary, this aspect of the present invention provides a membrane which can be prepared incorporating any antibody as a receptor for analyte detection, with minimum preparation of the antibody, The membrane of the present invention has the following advantages over existing devices that use antibody molecules:

1. The correct orientation of the antibody binding site is achieved for every antibody molecule by attaching it to an integral component of the self-assembled amphiphilic monolayer or bilayer film.

2. Density of receptor molecules in the membrane can be controlled and hence optimized for the most sensitive detection of the desired analyte.

3. The membrane of the present invention prepared with anti-Fc species-specific receptor molecules enables the use of any antibody raised in the selected species to be used in the membrane without further preparation of the antibody into monoclonal fractions or $F(ab)_2$ or Fab fragments.

4. Electrical measurements provide quicker results of the binding assay by using a conducting solid support which detects changes upon antigen-binding and subsequent monolayer or bilayer phase disruption brought about by the aggregation of two or more antibodies bound to the same analyte.

In a fourth aspect the present invention consists in a device adapted for implantation in a mammalian body, the device being coated with a membrane comprising a closely packed array of self-asembling amphiphilic molecules in which at least a proportion of the self-assembling amphiphilic molecules comprise a receptor molecule conjugated with a supporting entity, the receptor molecule having a receptor site, the receptor molecule being selected from the group consisting of antibodies and antibody fragments; the supporting entity being selected from the group consisting of a lipid head group, a hydrocarbon chain(s), a cross-linkable molecule and a membrane protein; the supporting entity being conjugated with the receptor molecule at an end remote from the receptor site and in a manner such that the receptor site is at or projects from a surface of the membrane remote from the device, the receptor molecule being such that either the attachment of specific cells to the membrane is enhanced or avoided.

In a preferred embodiment of this aspect of the present invention the membrane also includes a plurality of ion channels. It is preferred that the ion channel are peptides which form a β helix, and are most preferably gramicidin.

In a further preferred embodiment of the second aspect of the present invention the receptor molecules are F(ab)$_2$ or Fab fragments. It is also preferred that the receptor molecules are directed against fibronectin, vitronectin, endothelial cells, or epithelial cells, and most preferably fibronectin.

In a further preferred embodiment of the present invention, the membrane is attached to the device by providing groups on the membrane reactive with the surface of the device or with groups provided thereon.

In yet a further preferred embodiment of the present invention, the receptor molecules are either F(ab)$_2$ or Fab fragments which are linked to the supporting entity via their terminal sulfhydryl group.

In another preferred embodiment of the present invention, the amphiphilic molecules and the ion channels and/or receptor molecule supporting entity conjugate are provided with cross-linkable moieties in a manner such that each cross-linkable moiety is cross-linked to the cross-linkable moiety on another molecule.

At present it is preferred that the biocompatibility of the device is enhanced by using amphiphilic molecules naturally occurring in the mammalian species into which the device is to be implanted, or derivatives of these amphiphiles or synthetic amphiphiles, provided with a thiol group for attachment to metal surfaces such as palladium, titanium, platinum, silver or gold. Use of such amphiphiles tends to decrease the degree of host-device rejection. It is also preferred that the antibodies or antibody fragments are also derived from the mammalian species into which the device is to be implanted, as this will also result in a decreased level of host-device rejection. Alternatively the antibodies for antibody fragments are modified to reduce rejection e.g. humanization.

It is believed that attachment of epithelial or endothelial cells can be facilitated by the coating of the implantable device with the self-assembled monolayer or bilayer of polymerized or non-polymerized amphiphiles which incorporate orientated acylated antibodies or antibody fragments. The use of antibodies or antibody fragments raised against cell surface attachment proteins such as fibronectin or vitronectin should result in the coated implantable device binding epithelial or endothelial cells, thereby facilitating adhesion. Such a device coated with epithelial or endothelial cells will present a non-foreign surface to the body, preventing potential platelet adhesion which leads to thrombosis or tissue build-up. The cell-surface binding can also act as a seal to prevent infection spreading along a catheter inserted into the body. Anti-fibronectin antibodies and other antibodies against epithelial or endothelial cells are known in the art and tend to be species-specific.

As stated above, it is preferred that the self-assembled monolayer or bilayer is comprised of amphiphiles based on or derived from naturally occurring lipid molecules. Specific covalent linkage of the antibody or antibody fragments to the amphiphile ensures that each antibody binding site is correctly orientated such that all sites are accessible for binding to the antigen, and binding density can therefore be controlled.

A further advantage of the present invention is that the provision of ion channels in the membrane enables the passage of ions through the membrane to the device. Amphiphiles such as lipids provide a biocompatible matrix for the coating of the implantable device which is rendered permeable to charge transfer by the incorporation of ion channels. A number or ion channels may be used, however, at present the ion channel gramicidin, and in particular, gramicidin A and analogues thereof are preferred.

The incorporation of an ion channel such as gramicidin A may also render the surface of the implantable device antibacterial due to the bactericidal activity of gramicidin.

The presence of anti-epithelial or anti-endothelial antibodies in the self-assembled monolayer or bilayer consisting of amphiphiles and ion channels can prevent platelet adhesion or tissue build-up on the implanted device while at the same time still being permeable to charge transfer processes. Therefore, such a membrane can be used in conjunction with implantable devices which contain electrodes such as pacemaker leads and other devices which rely on charge transfer for detection or application while needing to present a non-thrombotic surface free from tissue build-up.

As will be appreciated by those skilled in the art, the conductance of the membrane of the first aspect of the present invention is dependent on the presence of the analyte due to the gating of the ionophores. This gating occurs due to displacement of the ionophores in one layer relative to the ionophores in the other layer following binding of the analyte to the receptor molecules. Three displacement gating mechanisms are possible and these have been designated "local disruption gating", "extended displacement gating" and "vertical disruption gating".

In order that the nature of each of these gating mechanisms may be more clearly understood, preferred embodiments of the first aspect of the present invention will now be described with reference to the accompanying drawings, in which.

Figure 1A:
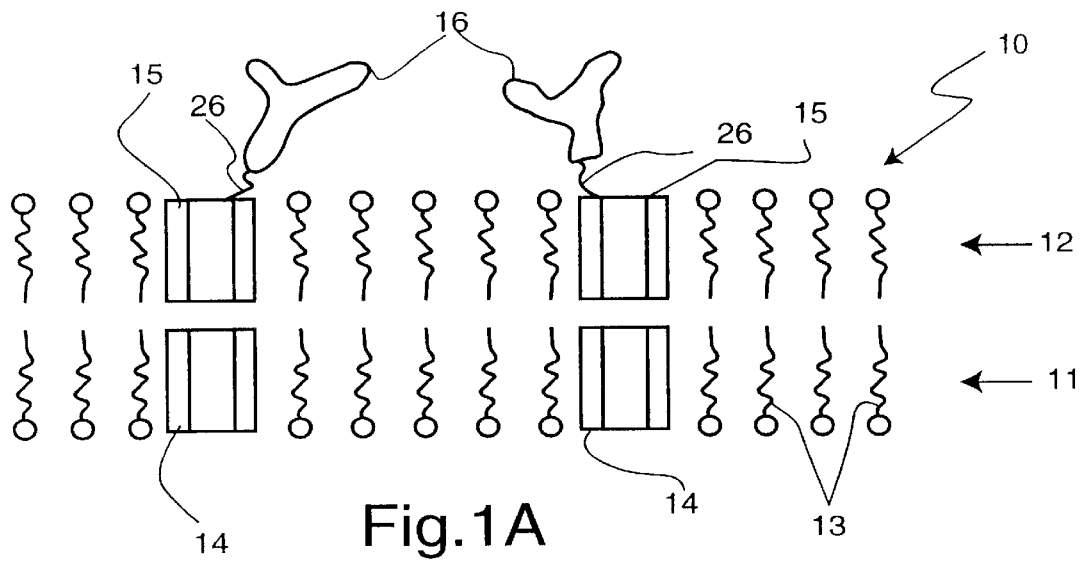
FIG. 1 shows a schematic representation of a membrane of the first aspect of the present invention in which the binding of the analyte results in a decrease in conductivity of the membrane due to local disruption gating.

As can be seen in FIG. 1 the membrane 10 consists of a first layer 11 and second layer 12 each comprising an array of amphiphilic molecules 13. Provided in first layer 11 are ionophores 14 and in second layer 12 ionophores 15. Attached to an end of ionophores 15 via linker group 26 are receptor molecules 16. In the absence of analyte (the situation shown in FIG. 1a) intact channels are formed due to the alignment of ionophores 14 and 15 through which ions may flow across the membrane.

Figure 1B:
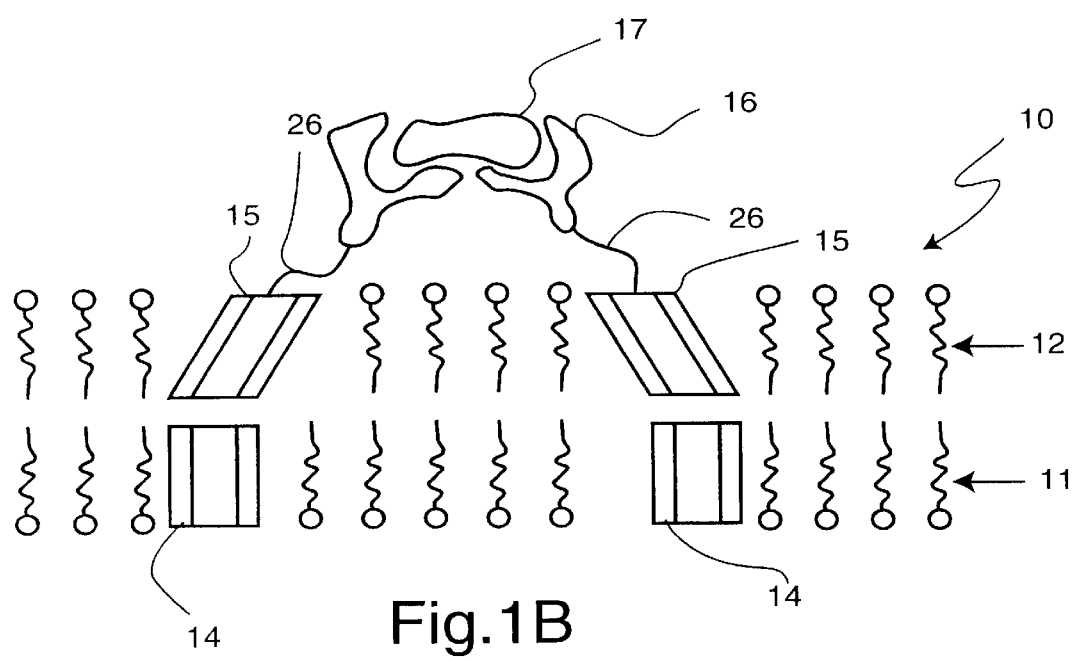

As is shown in FIG. 1b, upon the addition of analyte 17, the analyte 17 is bound to receptor molecules 16. This results in a cross-linking which causes a disturbance of alignment of ionophores 14 and 15, thereby preventing the flow of ions across the membrane by the ionophores 14 and 15.

Figure 2A:
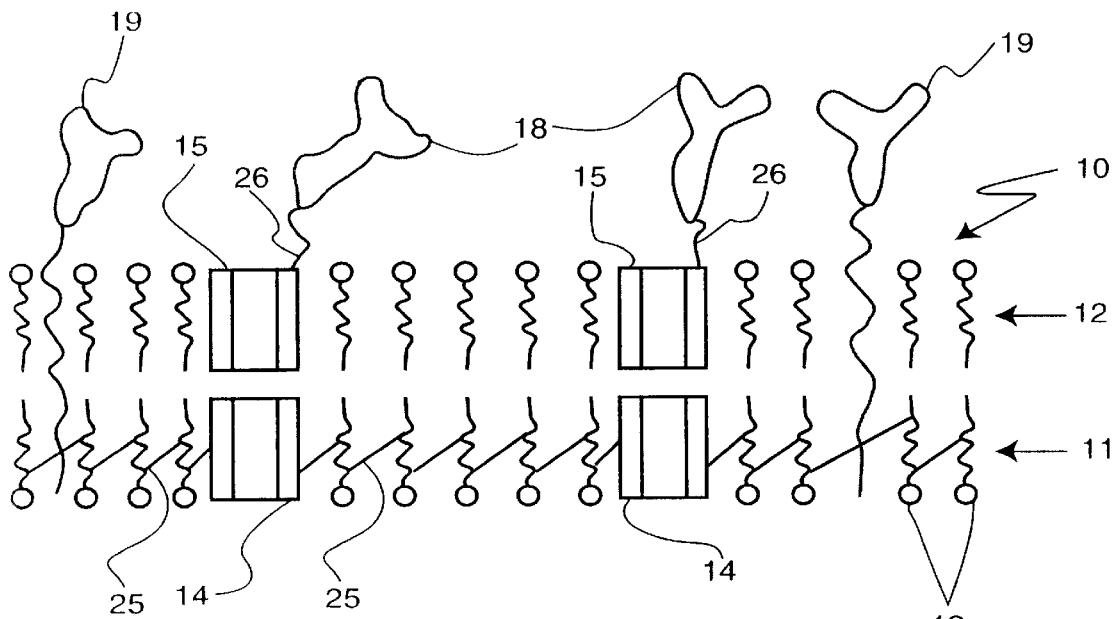
FIG. 2 shows a schematic representation of a membrane of the first aspect of the present invention in which the presence of an analyte results in a decrease in the conductivity of the membrane due to extended displacement gating.

As can be seen in FIG. 2 the membrane 10 consists of a first layer 11 and a second layer 12 composed of amphiphilic molecules 13. Provided in first layer 11 are ionophores 14 which are prevented from lateral diffusion within the first layer 11 due to cross-linking shown generally as 25. Ionophores 15 are provided in second layer 12. Attached to an end of ionophore 15 via linker group 26 is a first receptor 18 and included within second layer 12 is a second receptor 19 which is also prevented from diffusing laterally. In the absence of analyte (the situation shown in FIG. 2a) intact channels are formed due to the alignment of ionophores 13 and 14 through which ions may flow across the membrane.

Figure 2B:
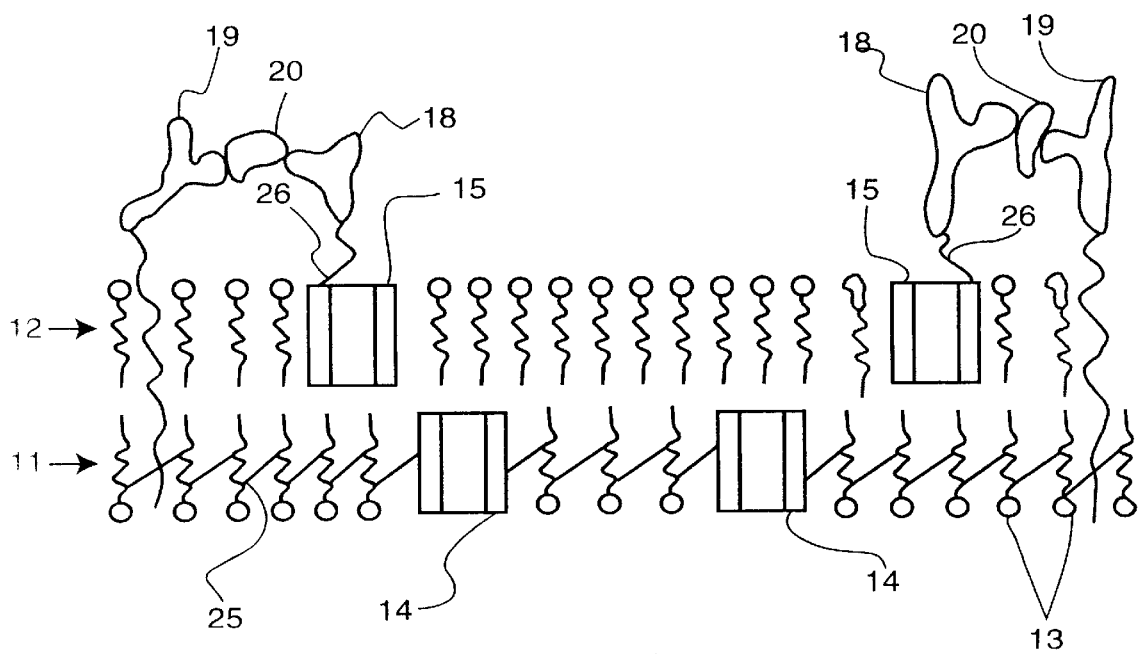

Upon the addition of analyte 20 these intact channels are broken. As can be seen in FIG. 2b the analyte 20 binds to first receptor 18 and second receptor 19. As second receptor 19 is prevented from diffusing laterally within second layer 12, the binding of first receptor 18 to analyte 20 which is bound to second receptor 19 causes the movement of ionophore 15 out of alignment with ionophore 14. This is referred to "extended displacement gating".

Figure 3A:
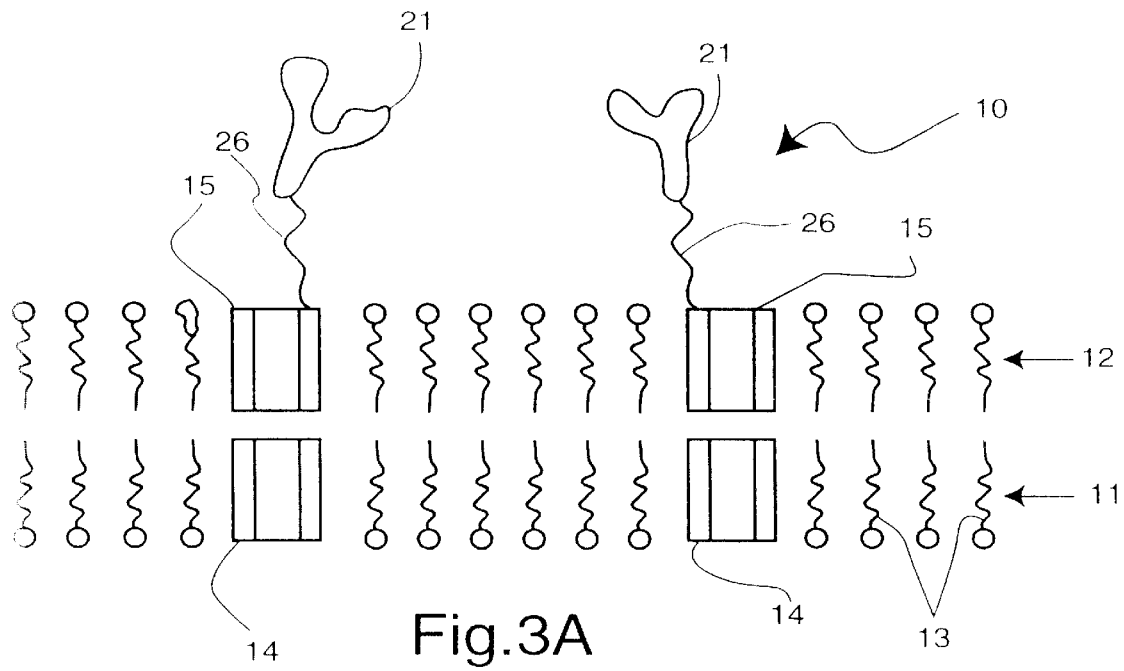
FIG. 3 shows a schematic representation of a membrane of the first aspect of the present invention in which the presence of an analyte results in a decrease in conductivity of the membrane due to vertical disruption gating.
Figure 3B:
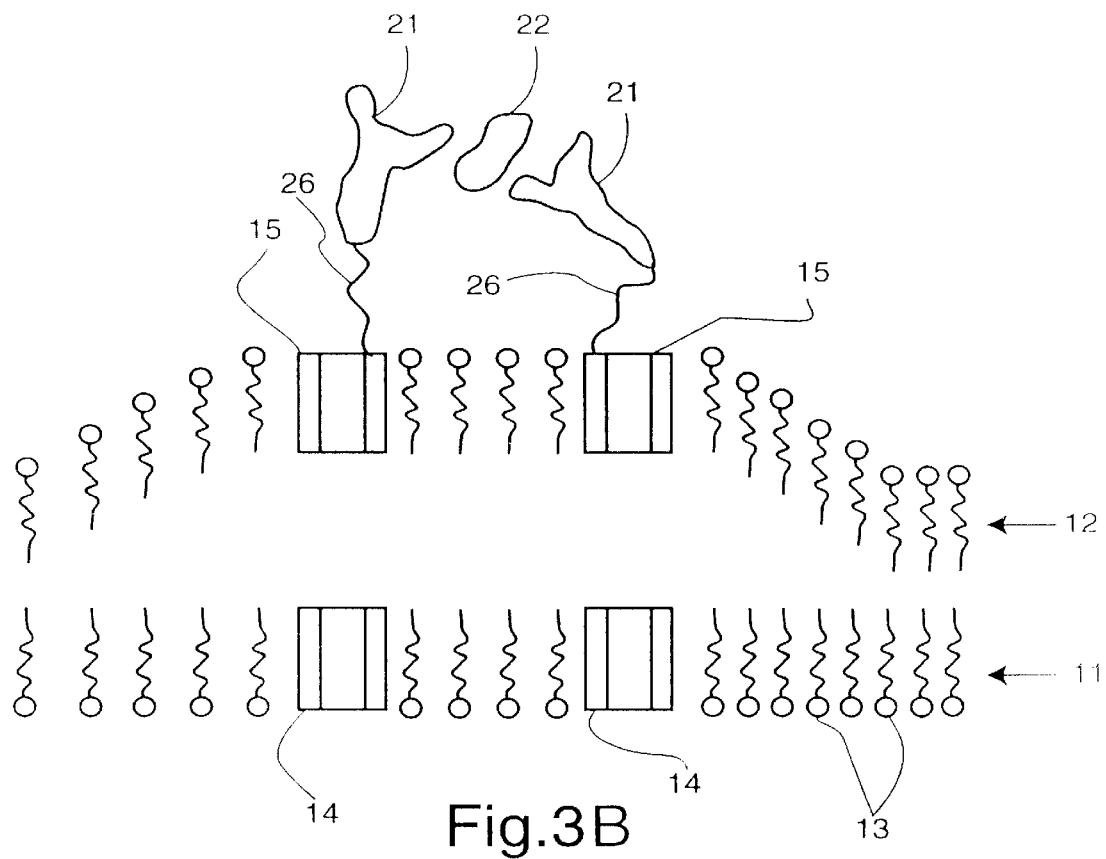

As can be seen in FIG. 3 the membrane 10 consists of a first layer 11 and second layer 12 composed of amphiphilic molecules 13. Provided in first layer 11 are ionophores 14 and in second layer 12 ionophores 15. Attached to an end of ionophore 15 via linker group 26 is a receptor molecule 21. In the absence of analyte intact channels are formed due to the alignment of ionophores 14 and 15.

Upon the addition of analyte 22 ionophores 15 and the second layer 12 are pulled away from ionophores 14 and first layer 11. This production of a space between the first layer 11 and second layer 12 results in channels no longer capable of allowing the passage of ions across the membrane. This form of gating is referred to as vertical displacement gating.

Figure 4A:
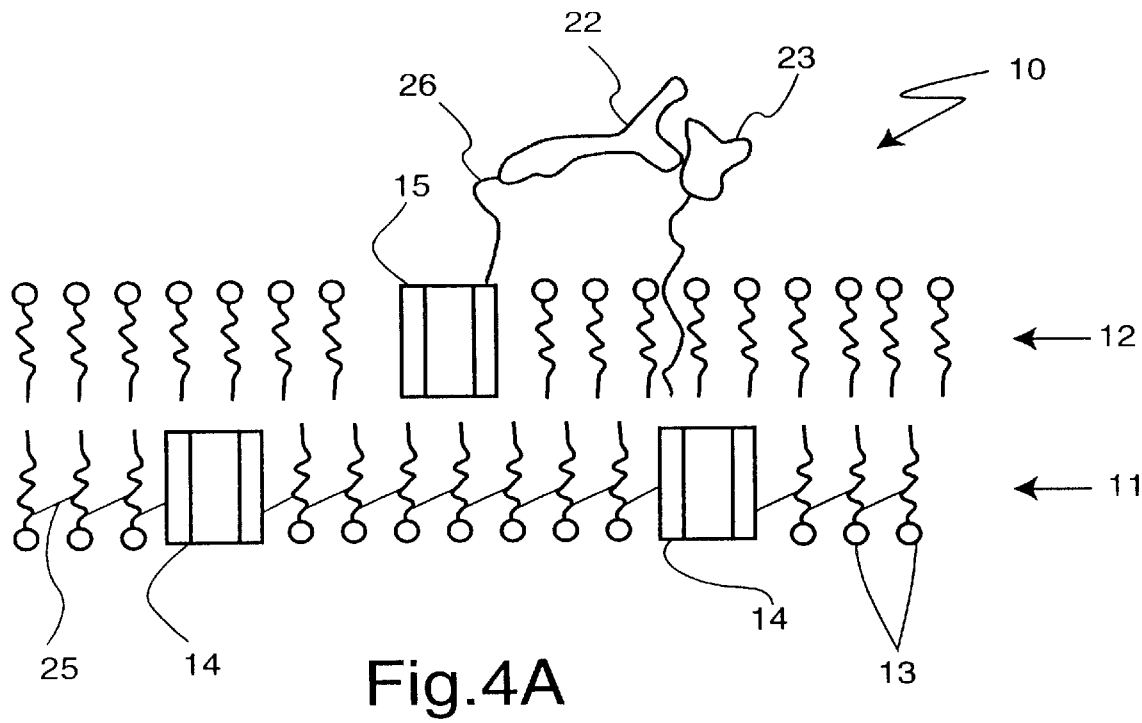
FIG. 4 shows a schematic representation of a membrane of the first aspect of the present invention in which the presence of the analyte results in an increase in the conductivity of the membrane due to extended displacement gating.

An alternate arrangement involving extended displacement gating is shown in FIG. 4. As can be seen in FIG. 4a the membrane 10 consists of a first layer 11 and second layer 12 comprising amphiphilic molecules 13. Provided in the first layer 11 are ionophores 14 which are prevented from lateral diffusion within the first layer 11 due to cross-linking shown generally as 25. Ionophores 15 are provided in second layer 12. Attached to an end of ionophore 15 via linker group 26 is a first receptor 22 and included within second layer 12 is a second receptor 23. In the absence of analyte (the situation shown in FIG. 4a) ionophores 14 and 15 are out of alignment due to the first receptor 22 being bound to second receptor 23. In this case the second receptor 23 is the analyte to be detected or an analogue thereof.

Figure 4B:
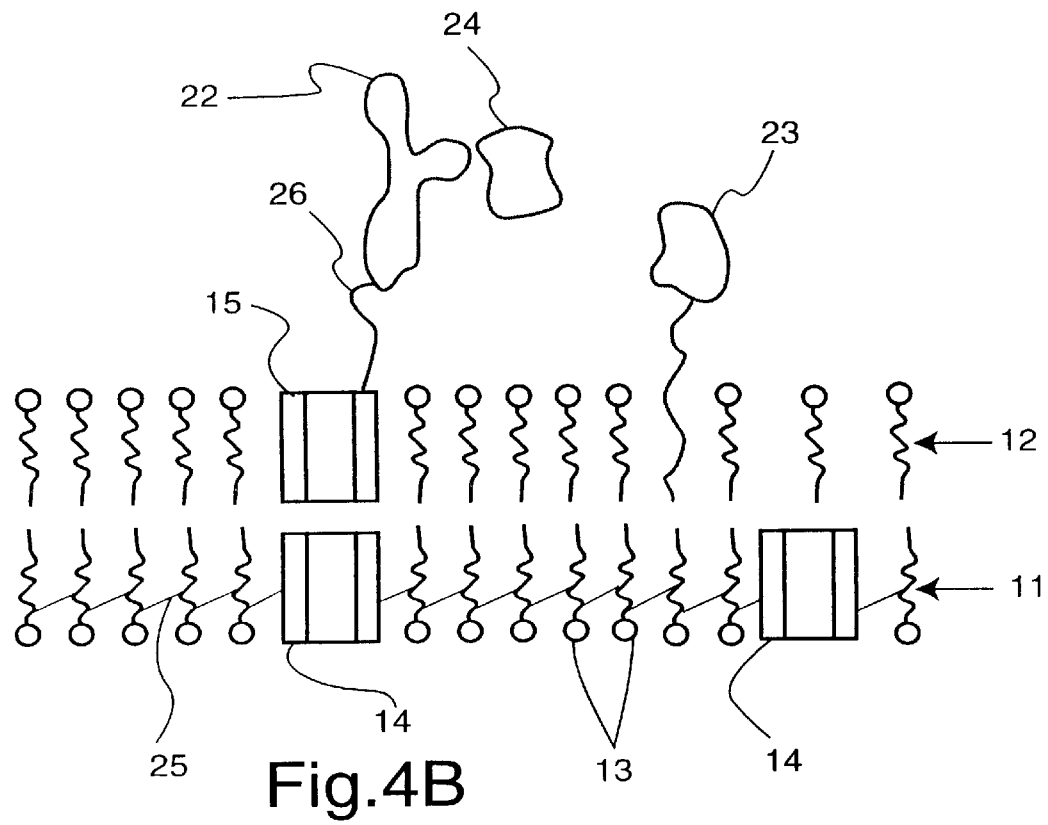
Figure 5:
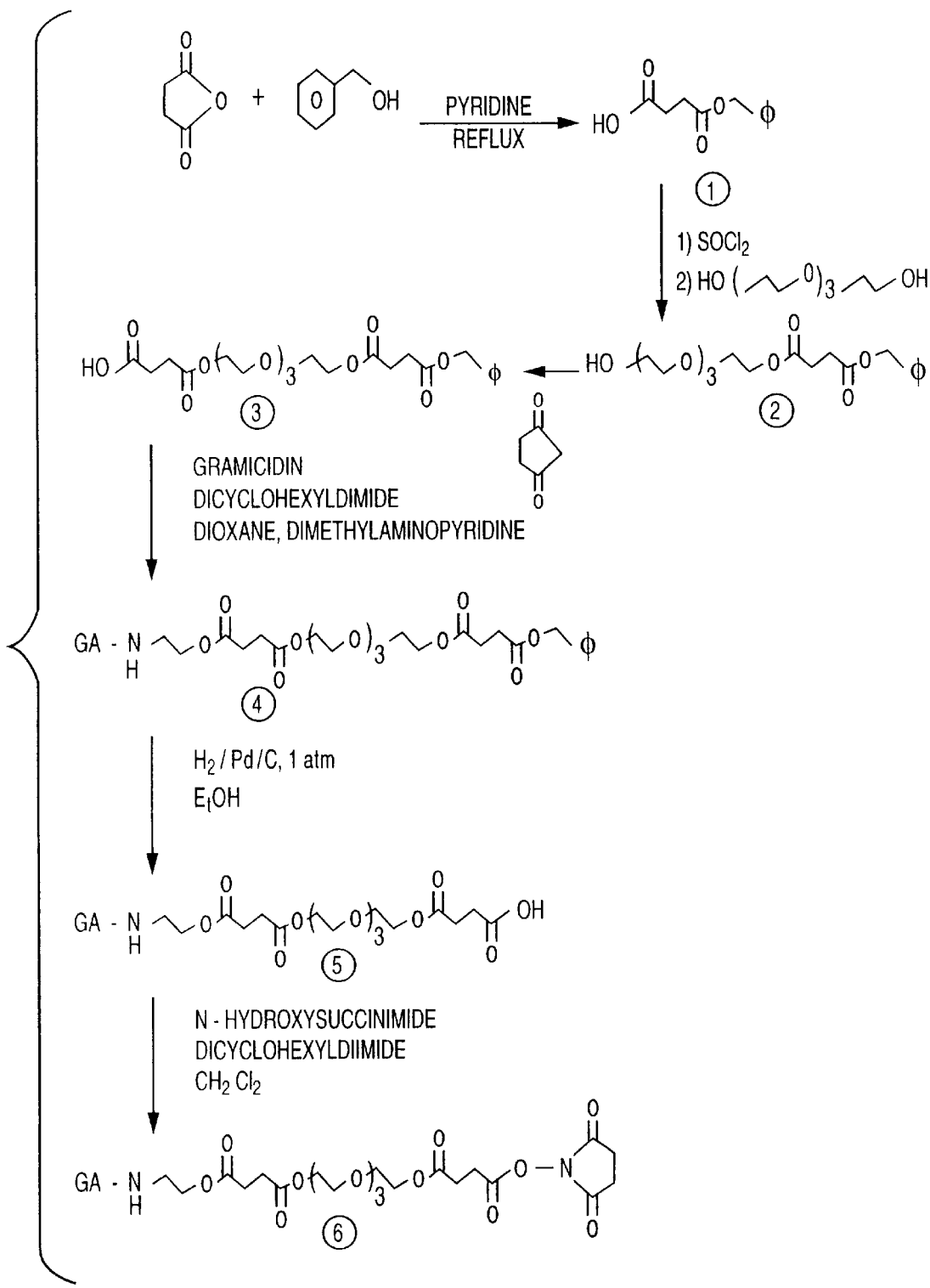
FIG. 5 shows the reaction scheme used to produce modified gramicidin.

As is shown in FIG. 4b, upon addition of analyte 24, by competitive binding, the first receptor 22 is released from second receptor 23 and ionophore 15 moves back into alignment with ionophore 14 thereby creating an intact channel which enables ions to flow across the membrane via ionophores 14 and 15.

In order that the nature of the present invention may be more clearly understood, preferred forms thereof will now be described with reference to the following examples:

EXAMPLE 1

Linker-Gramicidin

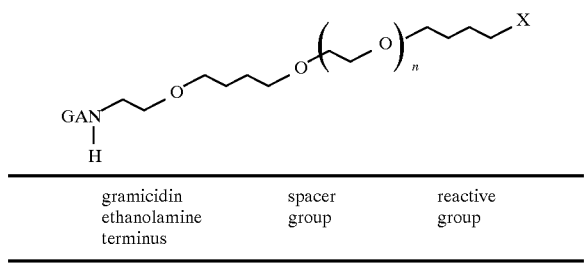

| gramicidin ethanolamine terminus | spacer group | reactive group | spacer group can consist of hydrocarbon, oligomers of ethylene glycol, oligopeptides etc. of such a length that gramicidin is able to conduct ions when the receptor molecule is coupled.

reactive groups can consist of N-hydroxysuccinimide esters or other common activated ester for covalent coupling to amine groups on proteins, hydrazine derivatives for coupling onto oxidised sugar residues, or maleiimide derivatives for covalent attachment to thiol groups, biotin, streptavidin or antibodies.

Synthesis of a Modified Gramicidin for Protein Attachment

1. Compound 1 (see scheme 1)

Succinic anhydride (2 g) and benzyl alcohol (2.2 g) were dissolved in pyridine (10 ml) and heated at 45° for 18 h. The cooled mixture was poured onto hydrochloric acid (1M, 200 ml) and extracted with dichloromethane (3×50 ml). The combined $CH_2Cl_2$ extracts were dried ($Na_2SO_4$) and evaporated to give compound 1 as a white solid (2 g).

2. Compound 2

Compound 1 (2 g) was stirred with 80 thionylchloride (10 ml) for 3 h. at room temperature. Excess thionylchloride was distilled and the residue was treated with tetraethylene glycol (25 ml) and pyridine (20 ml) and stirred for 24 hours. The mixture was poured onto hydrochloric acid (1M, 300 ml) and extracted with $CH_2Cl_2$ (3×50 ml). The combined $CH_2Cl_2$ extracts were dried ($Na_2SO_4$) and evaporated. The residue was filtered through a small plug of silica gel using ethyl acetate eluent to give the product as a pale yellow oil (1.2 g).

3. Compound 3

Compound 2 (0.5 g) and succinic anhydride (0.2 g) were mixed in pyridine (2 ml) and stirred for 24 h. The mixture was poured onto hydrochloric acid (1M, 100 ml) and extracted with dichloromethane (3×30 ml). The combined $CH_2Cl_2$ extracts were dried ($Na_2SO_4$) and evaporated to give compound 3 as a pale yellow oil (0.5 g).

4. Compound 4

Gramicidin (0.112 g), compound 3 (0.307 g), dicyclohexyldinimide (0.13 g), and a catalytic amount of 4-(N,N-dimethylamino)-pyridine were mixed in dry dioxane (10 ml) and stirred for 24 h. Excess dioxane was removed under reduced pressure and the residue was chromatographed on silica gel (dichloromethane/methanol/water/triethylamine 400:42:4:1 eluent) to yield the product as a white solid (0.53 g).

5. Compound 5

Compound 4 (0.02 g) was dissolved in ethanol and 10% palladium on charcoal was added. The mixture was then hydrogenated under hydrogen at 1 atm for 2 h. The mixture was filtered and the residue was chromatographed on silica gel (dichloromethane/methanol/water/triethylamine, 400:42:4:1 eluent) to yield the product as a white solid (0.19 g).

6. Compound 6

Compound (5) (0.019 g ) was dissolved in dichloromethane (3 ml) and dicyclohexyl carbodiimide (0.01 g) and N-hydroxysuccinimide (0.006 g) was added. The mixture was stirred for 24 h. and excess solvent was evaporated. The residue was taken up in ethanol and precipitated with water to give Compound 6 as a white solid (0.15 g).

Compound 7

Biotinylated Gramicidin A

A mixture of gramicidin A (49 mg, 27 $\mu$mol), N-BOC-glycine (48.5 mg, 277 $\mu$mol), dicyclohexylcarbodiimide (28.5 mg, 138 $\mu$mol) and 4-(N,N-dimethylamino)-pyridine (6.5 mg, 53 $\mu$mol) in dry, distilled dichloromethane (12 ml) was refluxed for 25 min. then allowed to cool to room temperature over 20 min. and evaporated to dryness under reduced pressure. The residue was chromatographed on a silica gel column eluted with dichloromethane/methanol/water/acetic acid (400:40:4:1) to afford a major U.V.-active fraction containing O-(N-BOC-glycyl)-gramicidin A (70 mg); $R_f$ ($CH_2Cl_2$/MEOH/$H_2O$/ACOH): 0.29.

O-Glycylgramicidin A

O-(N-BOC-glycyl)-gramicidin A (35 mg) was dissolved in redistilled trifluoroacetic acid (2 ml) under nitrogen and the solution was swirled for 5 min then evaporated to dryness. The residue was triturated with benzene (4 ml) then evaporated to dryness. The product was then chromatographed on a silica column eluted with dichloromethane/methanol/water/triethylamine (400:40:4:1) to a major, polar fraction of O-Glycylgramicidin A (33 mg).

O-(Biotinyl-$\epsilon$- aminocaproyl-glycyl) Gramicidin A

To a mixture of O-Glycylgramicidin A (16 mg) and biotinyl-$\epsilon$-aminocaproic acid N-hydroxy succinimide ester (3.5 mg) in dichloromethane/methanol (2:1, 1.5 ml) was added triethylamine (1 $\mu$l) and the mixture was stirred for 28 h then evaporated to dryness. The residue was chromatographed on a silica gel column eluted with dichloromethane/methanol/water (200:30:3) to afford O-(Biotinyl-$\epsilon$-aminocaproyl-glycyl)-gramcidin A (9 mg).

Attachment of Antibody to Conductive Gramicidin Channels via Streptavidin-Biotin Complex In order to use streptavidin as a linking element for attaching receptors to gramicidin ion channels, while still maintaining the conductivity of the channel it is clearly a prerequisite that the streptavidin molecule attached to the gramicidin-bound biotin have the adjacent biotin-binding site occupied to prevent crosslinking of the channel. Futhermore, a biotin-binding site on the opposite side of the streptavidin molecule must be maintained for attachment of the biotinylated receptor of choice. Such a configuration may be achieved in a variety of ways. One such protocol is as follows:

1. A black lipid membrane was formed from a solution of 50 mg/ml glycerol monooleate in N-decane with biotinylated gramicidin added to a concentration of 12.5 $\mu$M. The impedance of the BLM is shown in FIG. 6 as line 30.

Figure 6:
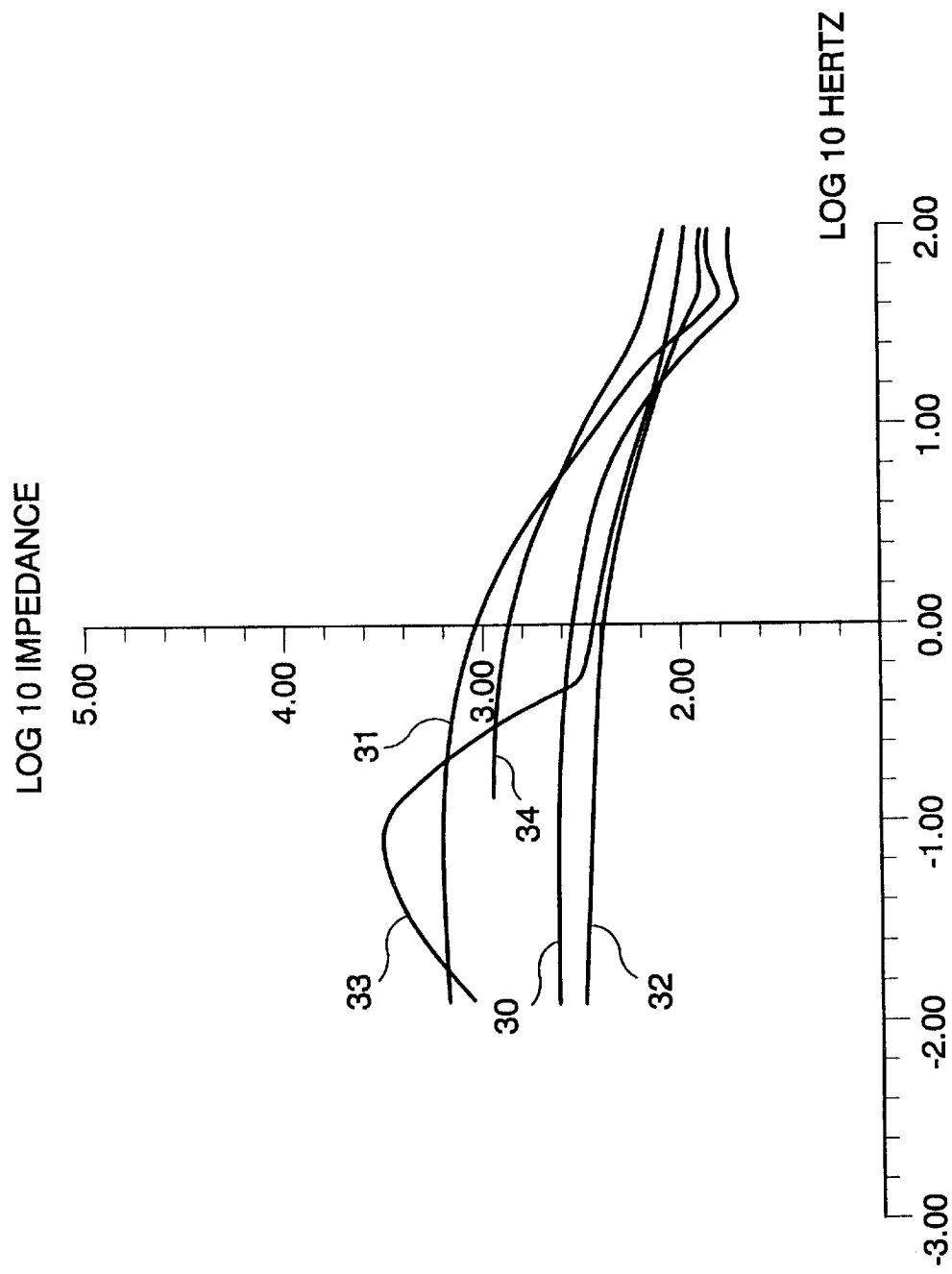
FIG. 6 shows the results of impedance measurements of the membrane of the first aspect of the present invention.

2. 10 $\mu$l of a preformed 1:1 complex of biotin/streptavidin was added to the BLM resulting in an increase in impedance as shown by line 31 in FIG. 6. A significant residual conductance remained, due to conducting biotinylated gramicidin channels.

3. 10 $\mu$l of anti-Fc antibody was added to the black lipid membrane. The binding of the anti-Fc antibody was evidenced by a concommittant decrease in membrane impedance shown as line 32 in FIG. 6.

4. 25 microliters of anti-HCG antibody was added to the black lipid membrane. The binding of the anti-HCG antibody to the anti-Fc antibody was evidenced by an increase in impedance shown as lines 33 and 34 in FIG. 6. This increase in impedance observed following the binding of the anti-HCG antibody is evidence of the gating of the gramicidin ion channels in the black lipid membrane.

EXAMPLE 2

N-Dansyl-dimyristoylphosphatidyl Ethanolamine

A mixture of dimyristoylphosphatidyl ethanolamine (65 mg, 0.102 mmol), dansyl chloride (37.5 mg) and triethylamine (15 $\mu$l) in chloroform/methanol (3:1, 4 ml) was stirred at room temperature for 24 h. then evaporated to dryness. The residue was dissolved in dichloromethane (30 ml) and washed with aqueous potassium bicarbonate solution (2.5% w/v, 20 ml). The organic phase was separated and the aqueous phase was extracted with dichloromethane (2×10 ml). The combined organic phases were dried ($Na_2SO_4$), filtered and evaporated to dryness. The residue was chromatographed on a silica column eluted with dichloromethane/methanol (9:1) to afford a yellow-fluorescent product (38 mg); $R_f$($CH_2Cl_2$/MEOH, 4:1)0.41.

EXAMPLE 3

Linker Lipids

N-4-(4-Maleimidophenyl)-butyryl-dimyristoylphosphatidyl Ethanolamine

To a solution of dimyristoylphosphatidyl ethanolamine (64 mg) and triethylamine 14 $\mu$l) in chloroform/methanol (4:1, 5 ml) was added solid 4-(4-maleimidophenyl)-butyric acid N-hydroxysuccinimide ester (48 mg) and the mixture was stirred at room temperature for 2 h. The mixture was evaporated to dryness then dissolved in chloroform (30 ml), washed twice with aqueous sodium chloride solution (1%, 20 ml), dried ($Na_2SO_4$), filtered and evaporated to dryness. The residue was chromatographed on a silica column eluted successively with chloroform, chloroform/methanol (95:5), chloroform/methanol (90:10) and chloroform/methanol (80:20) to afford the title compound (53 mg).

As would be appreciated by one skilled in the art, a range of other such linker lipids with varying reactive and spacer groups for attachment of receptors may be readily prepared (J. Connor, et al (1985) Pharmacol. Ther. 28, 341–365).

EXAMPLE 4

A generic surface for antigen binding can be produced by linking species-specific IgG anti-Fc antibody, antibody fragments or the Fc binding domain of an Fc receptor to a monolayer or biolayer of self-assembly amphiphilic molecules, orientated such that the anti-Fc molecules binding sites were available for binding antibody molecules. Linking the anti-Fc molecule can be carried out using a variety of linkers attached to either membrane proteins such as gramicidin or to lipids (as illustrated by Examples 1 and 3). The biolayer of self-assembling amphiphilic molecules can be produced by liposomes, BLM or on a supported substrate.

This Example uses polyclonal anti-mouse IgG anti-Fc antibody as the anti-Fc molecule and unilamellar liposomes (small unilamillar vesicles) prepared from lipid amphiphilic molecules.

Briefly, small unilamellar vesicles were prepared and fractionated using sonication and ultracentrifugation (C. Huang (1969) Biochemistry 8, 344–350; Y. Barenholz, D. Gibbes, B. J. Litman, J. Goll, T. E. Thompson, F. D. Carlson (1977) Biochemistry 16, 2806–10; J. Surrkuusk, B. R. Lentz, Y. Barenholz, R. L. Bittonen, T. E. Thompson (1976) Biochemistry, 15, 1393–1401; C. F. Schmidt, D. Lichtenberg, T. E. Thompson (1981) Biochemistry, 20, 4792–97).

Chromatographically pure egg yolk lecithin and cholesterol were dissolved in chloroform in a one-to-one ratio. The fluorescent lipid marker, Dansyl-PE, prepared as shown in Examples 2, was added to the mixture in a 1% mole ratio. Linker-gramicidin or linker lipid, prepared as shown in Examples 1 and 3 were added in a 1% mole ratio. Specifically, compound 6 in Example 1, the N-hydroxysiccinimide derivative of gramicidin, and compound 7 in Example 1, the biotin derivative of gramicidin, were the linker-gramicidin molecules used in separate experiments. The solvents were removed by vaccuum, and the lipids lyophilized from cyclohexane:methanol (95:5). The mixture was hydrated in 100 mM phosphate buffered saline, pH 7.9, and vortexed. Lipid dispersions were sonicated using a Branson sonifier (B-12) fitted with a cup horn sonifer, over ice for up to 30 min (3 min or 2 min cooling cycle). Small unilamellar vesicles were fractionated by ultracentrifugation at 180,000 g using a Beckman Ti 75 rotor at 10° C. for 90 min. Region III containing unilamellar vesicles was removed (Y. Barenholz, D. Gibbes, B. J. Litman, J. Goll, T. E. Thompson and F. D. Carlson, (1977) Biochemistry 16, 2806–10). Approximately 10% of the original material i.e. 1–5 µmoles total lipid, formed the Region III vesicles, as determined by the phospholipid concentration (G. R. Bartlett (1959) J. Biol. Chem. 234, 466–468) and dansyl-PE fluorescence, measured at 525 nm. Incorporation of GA or derivatives was determined by further fractionation of the vesicles on Sepharose CL4B and measuring GA's absorption at 280 nm of fractions containing the fluorescent dansyl-PE. The vesicle preparations were used immediately for the antibody conjugation procedure.

Anti-Fc antibodies were coupled to the linker-containing residues by the following method. Anti-mouse IgG polyclonal anti-Fc antibody and I-125 labelled anti-Fc antibody were added to the vesicles in 100 mM phosphate buffered saline, pH 7.9, at a concentration of 1–5 mg/ml. (If biotin was the reactive group of the linker on either gramicidin or lipid, streptavidin was added to the antibody in a 1:1 mole ratio, incubated at 37° C., 30', before adding to the vesicles.) The mixture was incubated at 20° C. for 12 hours and the anti-Fc antibodies linked to the vesicles was fractionated from unbound anti-Fc antibody by chromatography on Sepharose CL-4B. Anti-Fc antibody bound to vesicles was determined from the specific activities of I-125 labelled antibody and the fluorescent measurements of the Dansyl PE in the vesicles. The fractions containing anti-Fc antibody covalently attached to the vesicles were active when assayed by radioimmunoassay for antigen-binding activity, using mouse monoclonal IgG antibody.

SURFACE TREATMENT

EXAMPLE 5

A non-cytotoxic surface can be prepared by adsorbing amphiphilic molecules via a thiol moiety to a metal-coated surface, such as titaniam, palladium, platinum, gold or silver. The molecules may be naturally occuring lipids or their derivatives, such as phosphatidylcholines with terminal sulfhydryls (L. C. Coyl et al, 1989, Chemistry of Materials 1, 606–611) or synthetic thiol-bearing compounds such as alkanes (E. B. Troughton, 1988, Langmuir, 4, 365) or alkane derivatives bearing hydrophilic head-groups such polyethylene oxide.

In this example the alkane derivatives dodecane-thiol, polyethylene oxide-thiol and dodecane polyethylene oxidethiols were synthesized, absorbed from high-purity distilled ethanol to metal surfaces and tested for cytotoxicity.

Palladium-coated glass slides were prepared by sputtering palladium under vaccuum onto clean slides, and immediately transferred to distilled ethanol solutions of thiol lipids, such as 11-mecapto-3,6,9-trioxundecane-1-ol and 1-(1,2-dimyristoylglyceryl)-2-(11-mercapto-3,6,9-trioxaundecane-1-yl)-succinate, dodecane thiol. Resistance measurements of the thiol-lipid coated glass slides were carried out before the cytotoxicity tests were performed.

Cytotoxicity tests investigated the changes in cell count and cell morphology after 24 hr direct contact with the thiol-lipid coated glass slides, using bare glass and bare palladium-sputtered glass slides as controls. Sheep endothelial cells and mouse fibroblast cells, grown on 10% foetal calf serum were added to treated-styrene cell culture dishes containing the thiol-lipid coated glass slides. Each culture dish contained 30,000 cells/cm$^2$.

The slides were incubated at 36.5° C. for 24 hrs in an atmosphere-controlled oven. No evidence of cell death was shown by either viability staining or cell count. Both types of cells adherred to the thiol-lipid coated glass slides as successfully as their adhesion to the cell culture dish itself.

EXAMPLE 6

Antibodies raised against cell adhesion proteins such as vitronectin or fibronectin can be attached to the non-cytotoxic thiol-lipid coated glass slides as in Example 5 via amino acid side chains such as Arg, Lys, Asp, Glu or Cys using a cross-linkable molecule on the lipid that reacts with amino, carboxyl or sulfhydryl groups such as in Examples 1 and 3. Hence provide a non-cytotoxic surface which can bind endothelial or epithelial cells. Addition of gramicidin provides a surface with charge transfer capacity.

EXAMPLE 7

Membrane Gating

Apparatus

The black lipid membrane (BLM) apparatus consisted of two 10 cc chambers separated by a septum containing a 0.5 mm diameter hole. The chambers contained the BLM bathing solution and the hole in the teflon supported the BLM. One chamber was fitted with a glass window for the objective of a x10 microscope. The two chambers were fabricated of polyacrylamide (Perspex) and the septum was made from PTFE (Teflon). The chambers were held in place by teflon insulated stainless steel bolts. Gaskets made from reinforced medical grade silicon rubber were used between the perspex and teflon components. The membrane electrical impedance was measured using silver/silver chloride electrodes together with a List LM-EPC7 patch clamp amplifier and a computer controlled signal generator. The excitation was a sine wave swept in frequency from 0.1 Hz to 100 Hz. The voltage was set at 20 mV and the membrane current amplification was set at 0.5 mV/pA with the bandwidth limited to 1 kHz by a 6th order bandpass filter.

The apparatus was cleaned using distilled ethanol and distilled deionised water. Detergent should not be used for cleaning and all traces of detergent were removed. Traces of ethanol should be removed by pumping the components in a vacuum chamber. A 12.5 $\mu$M solution of biotynylated gramicidin in n-decane was prepared and 100 mg/ml of glycerol monoleate was added to the solution. A silicon rubber tube was fitted onto the end of a 50 microliter syringe, which was filled with about 10 microliters of the solution and used to wipe a film of lipid across the hole in the convex face of the septum. This film formed a BLM within a few minutes.

Titration Test of Lateral Segregation Gate

This series of measurements was designed to demonstrate the avidin-biotynylated gramicidin gate and also to demonstrate the gating mechanism. Streptavidin has four binding sites for biotin and the purpose of the titration study was to determine if more than one of these sites was required to disrupt the biontylated gramicidin channel. Measurements were made with a series of solutions of streptavidin in which none, one, two, three and four biotin binding sites were blocked with biotin.

Figure 7:
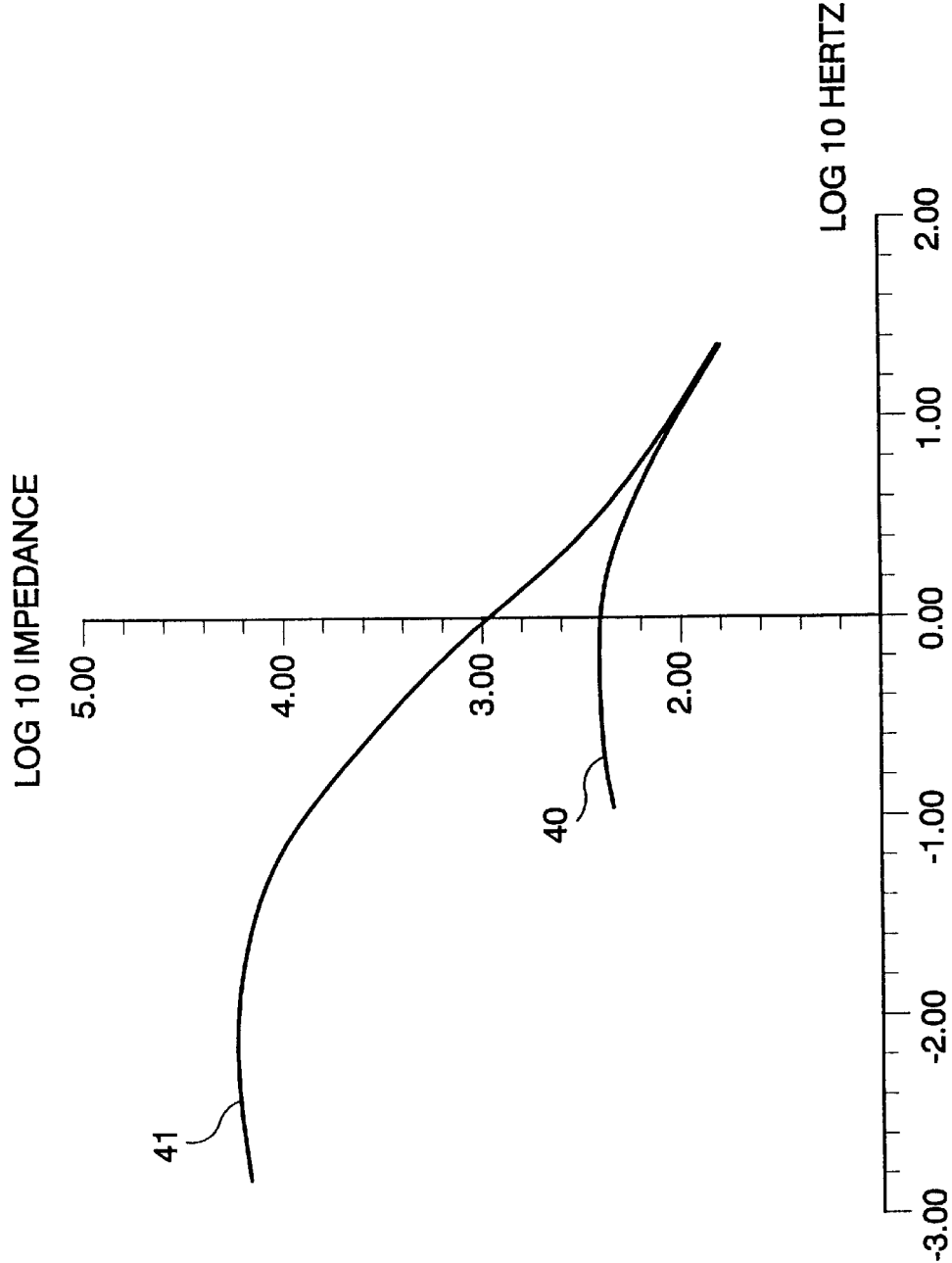
FIGS. 7 to 9 show the results of experiments demonstrating the gating of the membrane of the first aspect of the present invention.
Figure 8:
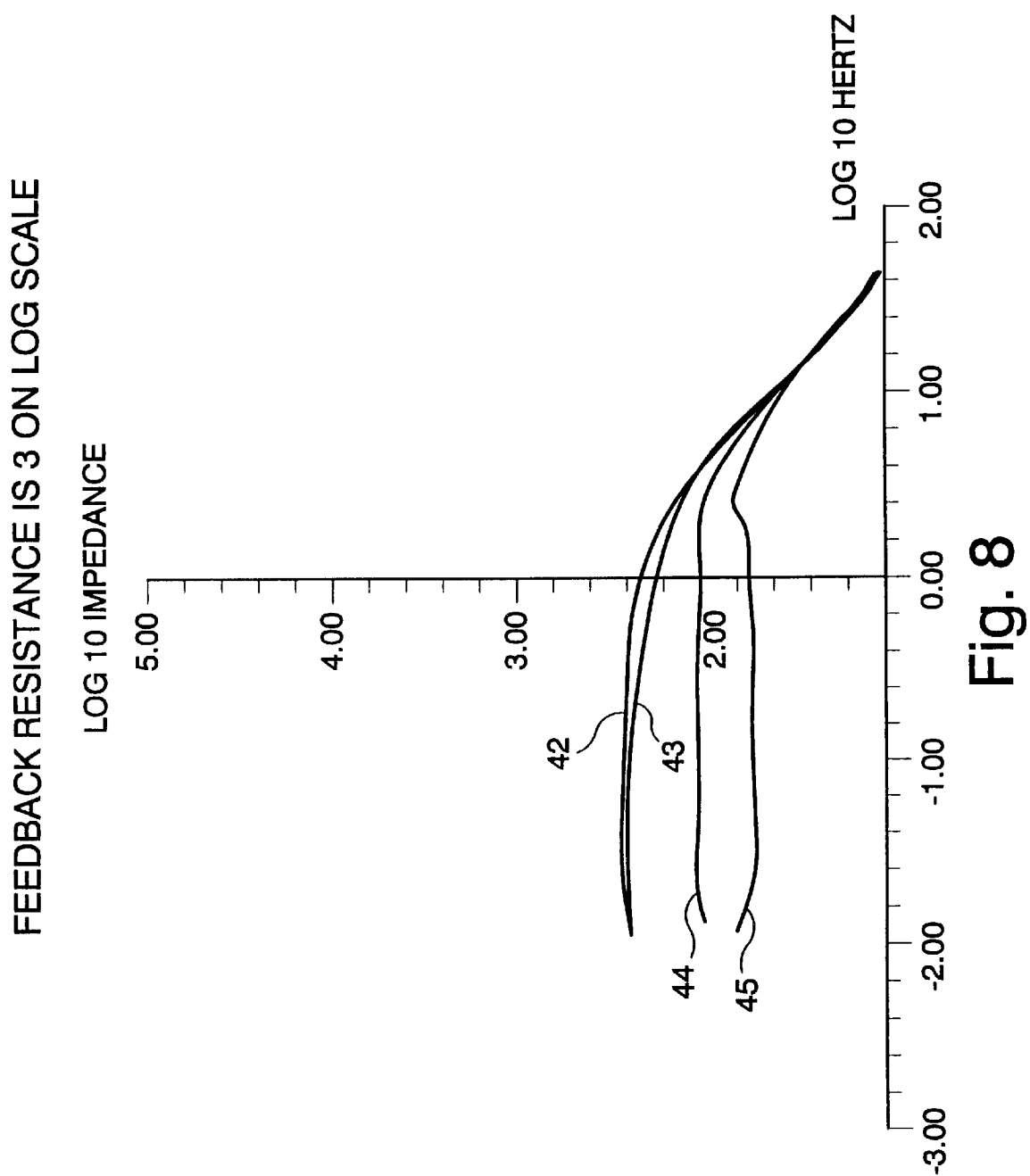
Figure 9:
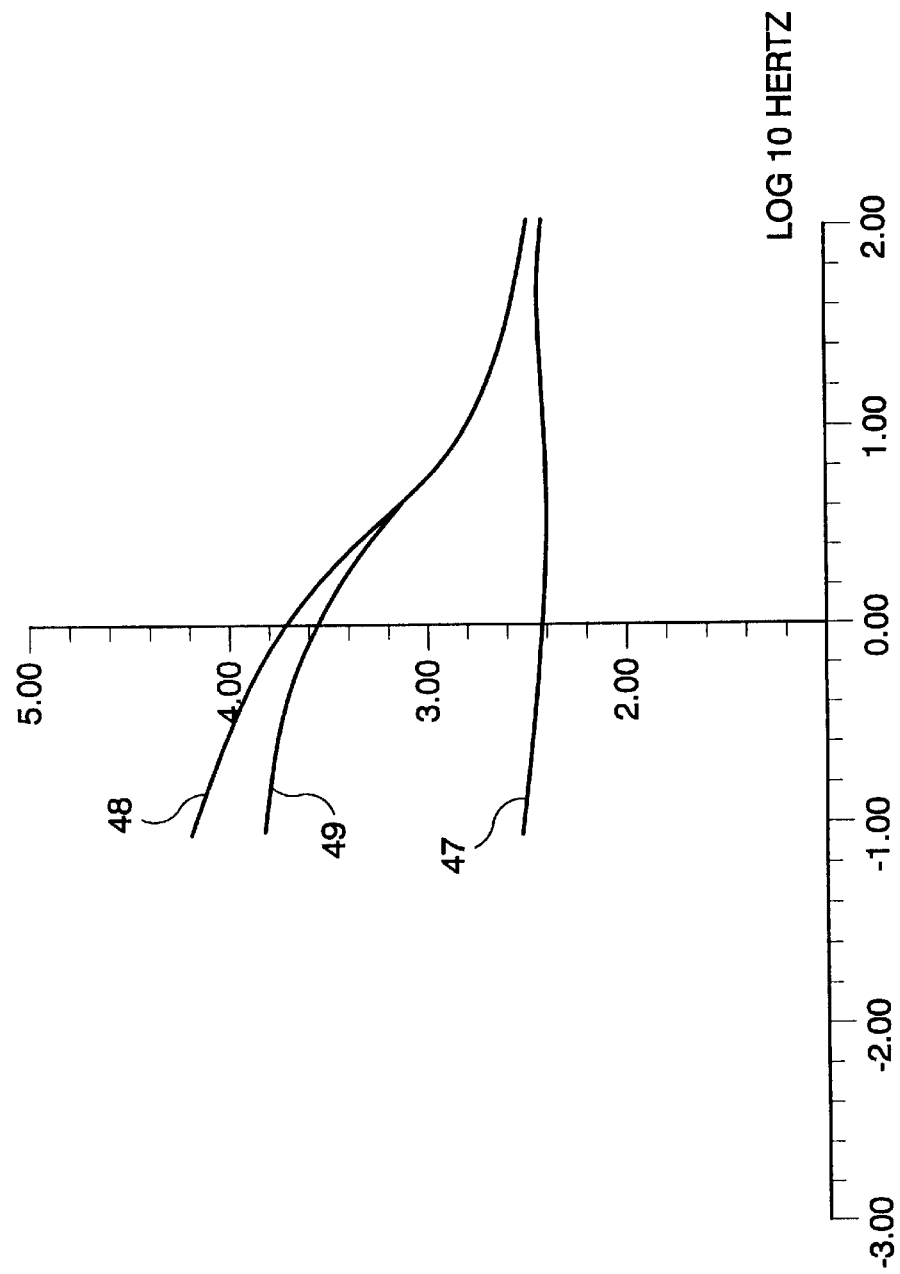

First a BLM was formed from a solution of glycerol monoleate (50 mg/ml) and biotynylated gramicidin (12.5 $\mu$M) in n-decane which results in an ionic conductance of about 250 megohms. The BLM was bathed in a 0.1M saline solution. Ten microliters, of mole ratios 4, 3.8, 3.6 and 3.2:1 biotin to streptavidin was successively added to the saline solution on one side only of the BLM. No increase in BLM impedance was observed. However, when streptavidin with no attached biotin was added to the solution on the other side the impedance increased from about 250 megohms to about 12,000 megohms. Similarly when a single addition of mole ratios 3.2:1 was added to a freshly made BLM the impedance increased from 250 megohms to 8,000 megohms as before. FIG. 7 shows the basic gate effect in which streptavidin is added to an ionically conducting BLM. In FIG. 7, line 40 shows the impedance of the BLM without streptavidin added and line 41 shows the impedance following addition of streptavidin. FIG. 8 shows the titration in which the 4:1 (line 43), 3.8:1 (line 44) and 3.6:1 (line 45) biotin-:streptavidin were added. Line 42 shows the impedance of the BLM containing biotinylated gramicidin which results in an ionic conductance of about 250 megohms. It should be noted that the impedance instead of increasing actually decreases. FIG. 9 shows the effect of adding 3.2:1 biotin-:streptavidin to a fresh BLM containing biotinylated gramicidin by itself. In FIG. 9 the impedance of the membrane incorporating biotinylated gramicidin is shown as line 47, the effect of addition of streptavidin is shown as line 48 and the effect of the 3.2:1 biotin:streptavidin is shown as line 49.

In each of these Figures the impedance spectra have logarithmically scaled axes with impedance on the ordinate and frequency on the abscissa. The impedance ranges from 10 megohms to 100 megohms with the line through 3.0 representing 100 megohms. The frequency ranges from 1 millihertz to 100 hertz with the line through 0.0 representing 1 hertz. Most of the impedance spectra consists of two distinct components, a 45° line at the high frequency end of the spectrum which is the capacitive component of the membrane and a horizontal line which represents its resistive component. At low impedances the resistive component can completely dominate the capacitive component. At high impedance changes in the capacitive component indicate changes in the morphology of the membrane while changes in resistance indicate changes in the ion channels through the membrane.

FIG. 7 shows a BLM formed from a solution of glycerol monooleate (50 mg/ml) and biotinylated gramicidin (12.5 $\mu$m) in n-decane which results in an ionic conductance of about 250 megohms line 40. Line 41 shows that adding 10 microliters of 1 mg/ml streptavidin solution to the solution on either side of the membrane, increases the impedance to about 12,000 megohms.

In FIG. 8, line 42 shows a BLM containing biotinylated gramicidin which results in an ionic conductance of about 250 megohms. Line 43 shows that adding streptavidin in which all the biotins sites have been blocked with biotin, does not bind the biotinylated gramicidin and makes no difference to the conductivity. Similarly lines 44 and 45 show that where the number of biotin binding sites on the streptavidin are less than two there is no increase in impedance i.e. no disruption of the gramicidin has occurred, however, the reduction in impedance demonstrates that binding has occurred. When unbiotinylated streptavidin was subsequently added to the solution on the same side of the BLM no further change in the impedance occurred giving a further indiction that binding had occurred without gating and that gating had to be due to a cross-linking rather than a single binding. All the above additions were to one side of the membrane only. When streptavidin was added to the other side of the BLM the conductance increased to about 12,000 megohms demonstrating that the ion channel gating mechanism was not effected by binding of streptavidin to the biotinylated gramicidin, i.e. competitive binding of the streptavidin was the only factor inhibiting the gaging effect.

In FIG. 9 lines 46 shows a BLM containing a biotinylated gramicidin which results in an ionic conductance of about 250 megohms. Line 47 shows the effect of adding biotinylated streptavidin prepared as a 3.2:1 biotin:streptavidin. This shows that a significant number of double binding sites are available with a ratio of 3.2:1. Line 47 shows the effect of subsequently added unbiotinylated streptavidin. The increase in impedance shown in line 47 over line 46 indicates that a significant number of streptavidin molecules were completely biotinylated with a ratio of 3.2:1 biotin-:streptavidin. This is as would be expected.

FIG. 6 shows the impedance spectra corresponding to preparation of a biosensing membrane and the change in spectra associated with the sensing of anti-HCG antibodies.

Streptavidin consists of four biotin-binding units which are arranged with the biotin-binding sites located in closely spaced pairs at opposite poles of the molecule. The effect of streptavidin on the conductance of a bilayer containing gramicidin with covalently attached biotin is herein shown to be dependent on whether one or both adjacent biotin-binding sites directed toward the bilayer are available to the gramicidin-linked biotins. A streptavidin biotin-binding site may be rendered unavailable by occupying it with a molecule of free biotin i.e. biotin not covalently attached to another species. It is expected that the addition of biotin to streptavidin will afford a binomial distribution of streptavidin species with 0, 1, 2, 3 or 4 bound biotins according to the ratio of biotin to streptavidin. This distribution is set out in Table 1.

TABLE 1

| Ratio Biotin: Streptavidin | % Streptavidin Species with | | | | |
|---|---|---|---|---|---|
| | 0 | 1 | 2 | 3 | 4 bound biotins |
| 0.1 | 100 | 0 | 0 | 0 | 0 |
| 1.1 | 31 | 42 | 21 | 5 | 1 |

TABLE 1-continued

| Ratio Biotin: Streptavidin | % Streptavidin Species with | | | | |
|---|---|---|---|---|---|
| | 0 | 1 | 2 | 3 | 4 bound biotins |
| 2:1 | 6 | 25 | 38 | 25 | 6 |
| 3:1 | 1 | 5 | 21 | 42 | 31 |
| 3.2:1 | 1 | 3 | 15 | 41 | 40 |
| 3.6:1 | 1 | 1 | 5 | 29 | 66 |
| 3.8:1 | 1 | 1 | 1 | 17 | 81 |

It is also evident that streptavidin with no bound biotins will contain only species with two adjacent binding sites and streptavidin with three bound biotins will contain only species with one biotin binding site while those with one or two biotins will contain mixtures of one and two adjacent biotin binding sites. Thus samples of streptavidin containing in excess of single binding sties over adjacent available binding sites can be prepared by adding large ratios of biotin to streptavidin.

EXAMPLE 8

Ferritin Gating in Presence or Absence of Tethered Receptor

Assembly of the Biosensor Membrane

Figure 10:
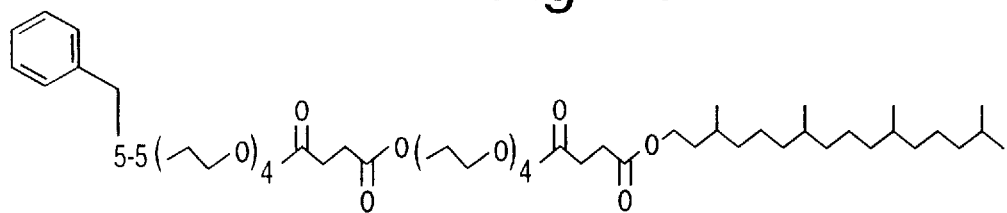
FIG. 10 shows linker lipid A.
Figure 11:
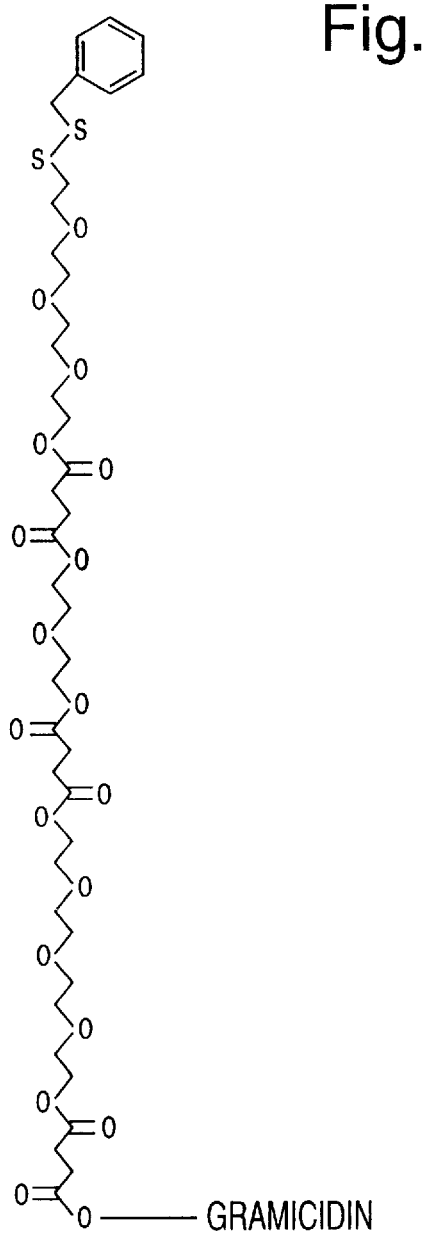
FIG. 11 shows linker gramicidin B.
Figure 12:
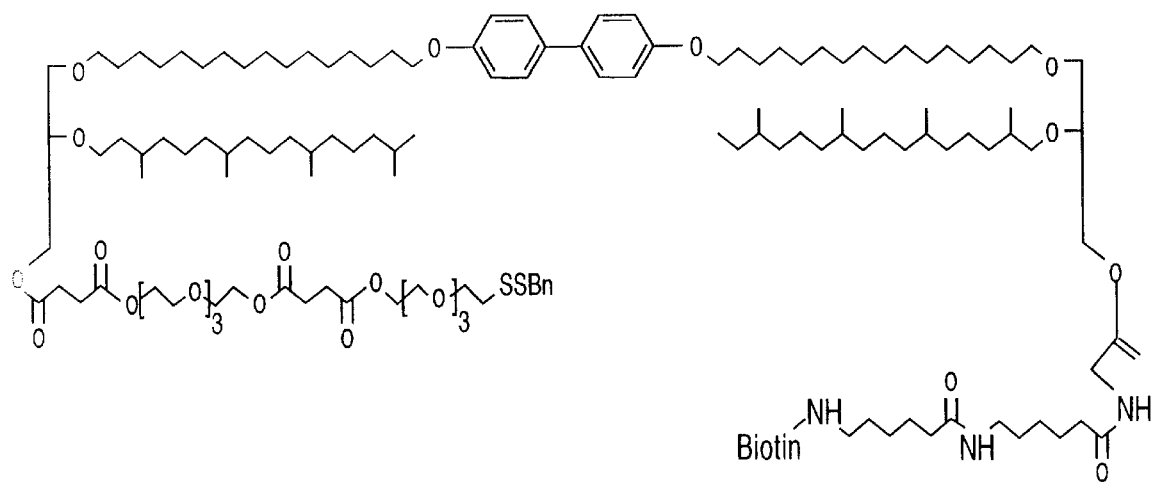
FIG. 12 shows membrane spanning lipid XXB.

Onto a clean glass of plastic slide, an adhesion layer of chromium (50 angstrom) followed by a gold layer (200–2000 angstroms) is evaporated. The freshly evaporated gold coated electrode is taken and immediately assembled into a teflon slide assembly holder such that an electrode surface is defined by a circular teflon well pressed onto the gold electrode. The teflon well forms a tight, water impermeable seal at the electrode perimeter. 5 µl of an ethanolic solution of glyceryl monophytanyl ether (10 mM), linker lipid A, FIG. 10 (1 mM), the disulfide of mercaptoacetic acid (0.8 mM), linker gramicidin B, FIG. 11 (0.1 µM), membrane spanning lipid XXB, FIG. 12 (1 µM), is added to each well. (Synthesis protocols for linker lipid A, linker gramicidin B, and membrane spanning lipid XXB are set out in WO 92/17788 published on Oct. 15, 1992 (corresponding to U.S. Ser. No. 08/119,116, filed Sep. 21, 1993, now U.S. Pat. No. 5,401,378, issued Mar. 28, 1995; Atty. Dkt. 47-53) and WO 94/07593, published on Apr. 14, 1994 (corresponding to U.S. Ser. No. 08/406,853, filed May 17, 1995, Atty. Dkt. 47-75). The gold coated electrode is left immersed in the solution for 5 minutes, and rinsed with ethanol before the second layer is added.

Figure 13:
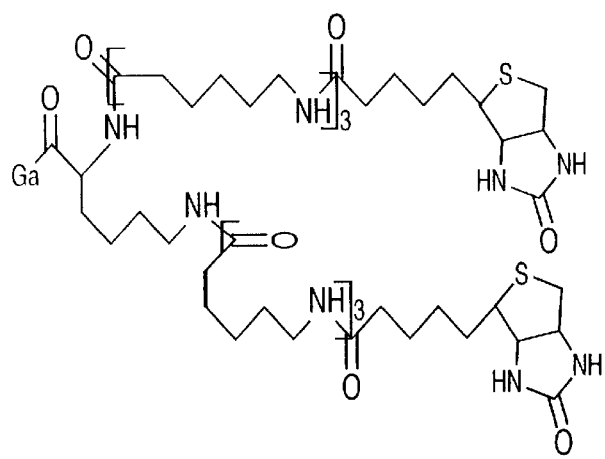
FIG. 13 shows Ga(XXXB)$_2$.

Formation of the second layer of the bilayer membrane is carried out by addition of 5 µl of a solution containing 28 mM of glyceryl monophytanyl ether and 0.28 µM Ga(XXXB)$_2$ (FIG. 13). The well assembly was then rinsed 2 times with phosphate buffered saline (PBS) resulting in the formation of the second lipid layer of the bilayer sensing membrane. The well assembly holds approximately 200 µl of PBS. Into this 200 µl of PBS in the well is placed a counter electrode a connection is made between this counter electrode and impedance bridge measuring apparatus. To complete the electrical circuit, the other connection is made between the gold electrode and the impedance bridge. Using the impedance bridge the conduction of the membrane may then be determined.

Ferritin Response

The ferritin detection is carried out using anti-ferritin antibody Fab' fragments attached to both the gramicidin channel and the tethered membrane spanning lipid C via a streptavidin-biotin linker.

Streptavidin (5 µl 0.5 mg/ml PBS) is added to the membrane and left to incubate 10–60 min, before rinsing out with PBS. Anti-ferritin Fab' fragments, biotinylated via the free thiol groups using standard methods, is added to the membranes (5 µl 0.05 mg/ml PBS), incubated 10–60 min, then rinsed out with PBS. Ferritin in PBS is added to the biosensor and the change in impedance response is recorded against time.

Figure 14:
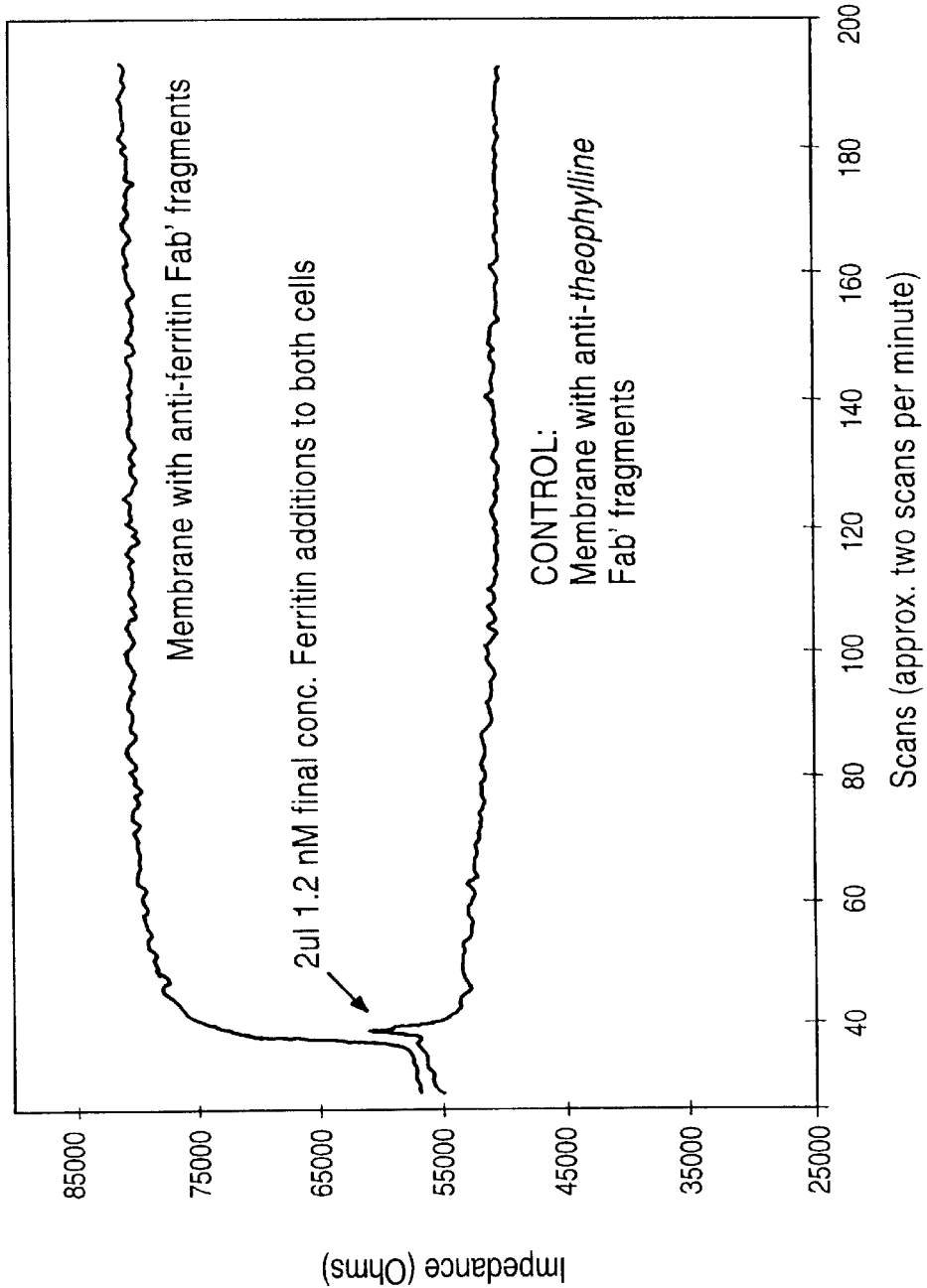
FIG. 14 shows comparison of response to ferritin challenge for membranes containing anti ferritin Fab' or anti theophylline Fab' fragments.
Figure 15:
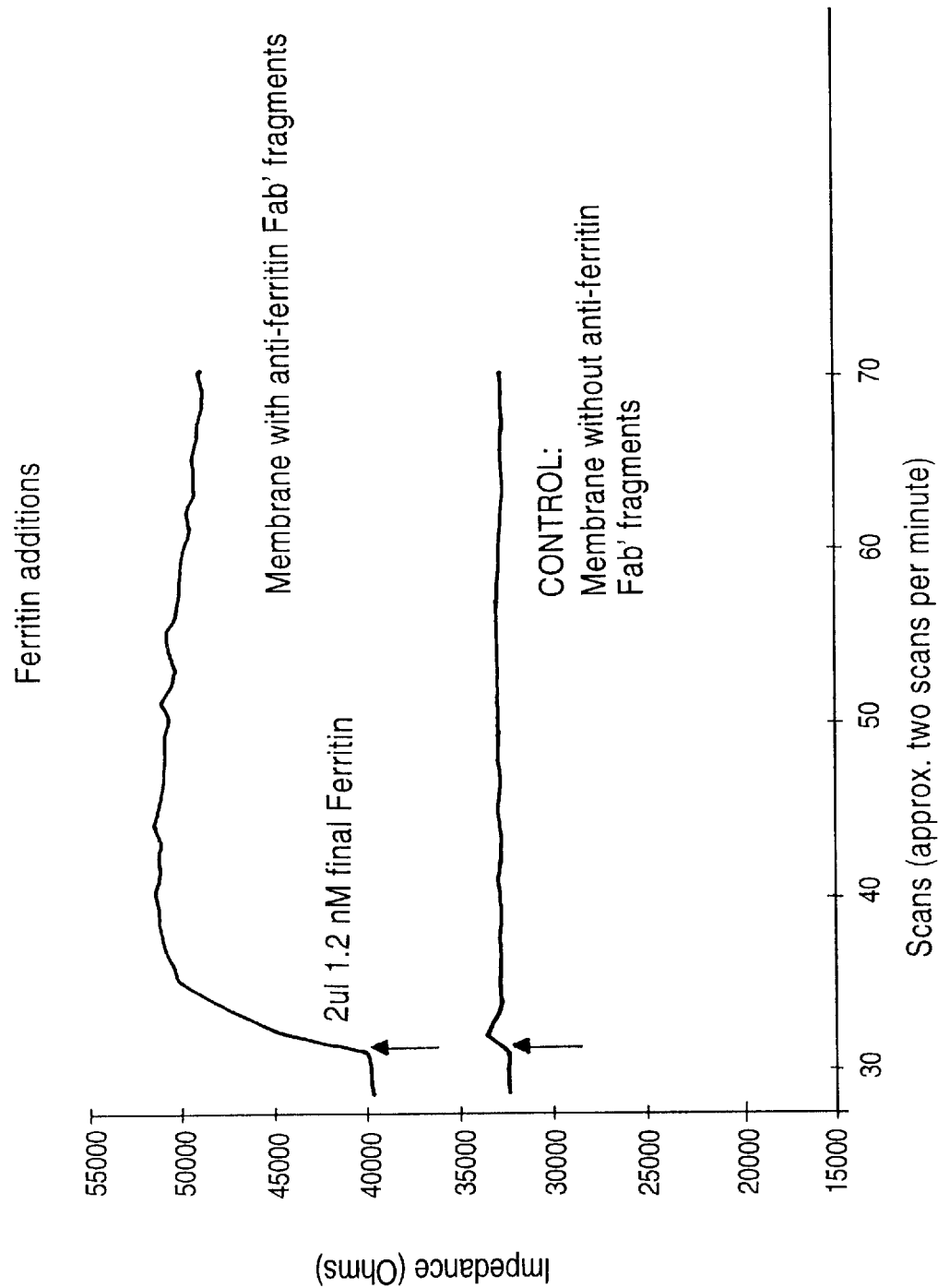
FIG. 15 shows ferritin response.
Figure 16:
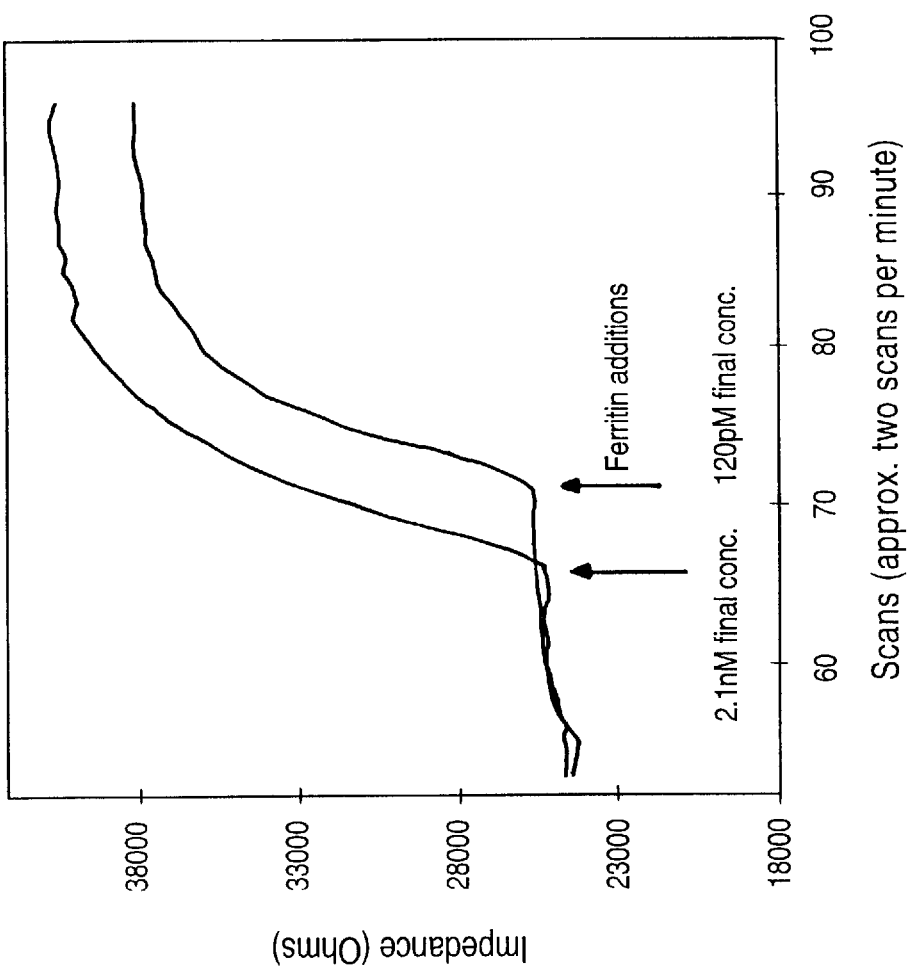
FIG. 16 shows detection of ferritin at two different concentrations.

FIGS. 14 and 15 show the ferritin response in the presence or absence of anti-ferritin Fab' fragments. The control membrane in FIG. 14 was prepared without Fab' fragments and shows no response to ferritin addition. The control membrane in FIG. 15 was prepared with anti-theophylline Fab' fragments (which show no specificity or selectivity toward ferritin) and hence did not respond to the addition of ferritin. FIG. 16 demonstrates the detection of ferritin at two different concentrations—$21 \times 10^{-9}$M and $120 \times 10^{-12}$M.

EXAMPLE 9

Theophylline Detection

Bilayer Assembly

Onto a clean glass to plastic slide, an adhesion layer of chromium (50 Angstroms) followed by a gold layer (200–2000 Angstroms) is evaporated. The freshly evaporated gold coated electrode is assembled onto a teflon slide assembly holder such that an electrode surface is defined by a circular teflon well (diameter=4 mm, volume=200 µl) pressed onto the gold electrode. The teflon well forms a tight, water impermeable seal at the electrode perimeter. Onto the electrode is dispensed a 2 µl aliquot of an ethanolic solution comprising linker lipid A (10 mM), the disulfide of mercaptoacetic acid (0.8 mM), linker gramicidin B (0.1 µM), and membrane spanning lipid XXB (1 µM), followed immediately by addition of ethanol (50 µl). The gold coated electrode is incubated with the solution for 30 minutes. The ethanolic solution is then removed from the well and the well is refilled with ethanol (50 µl). This process is repeated twice and the final ethanol wash is removed, leaving the well empty. This procedure forms the first layer of the bilayer sensor membrane and may be stored in ethanol, glycerol, ethylene glycol or other alcohol for several months. Formation of the second layer of the bilayer membrane is carried out by addition of 2 µl of an ethanolic solution of glyceryl monophytanyl ether (10 mM) and gramicidin-theophylline conjugate (0.1 µM), followed by phosphate buffered saline (PBS, 100 µl) and the well assembly is left for at least 30 minutes to equilibrate. The well assembly is then rinsed with PBS (2×100 µl), leaving the well filled and ready for use. Into the 100 µl of PBS remaining in the well is placed a counter electrode, a connection is made between this counter electrode and the impedance bridge measuring apparatus. To complete the electrical circuit, the other connection is made between the gold electrode and the impedance bridge. Using the impedance bridge the conduction of the membrane may ben be determined.

Antibody Response

Figure 17:
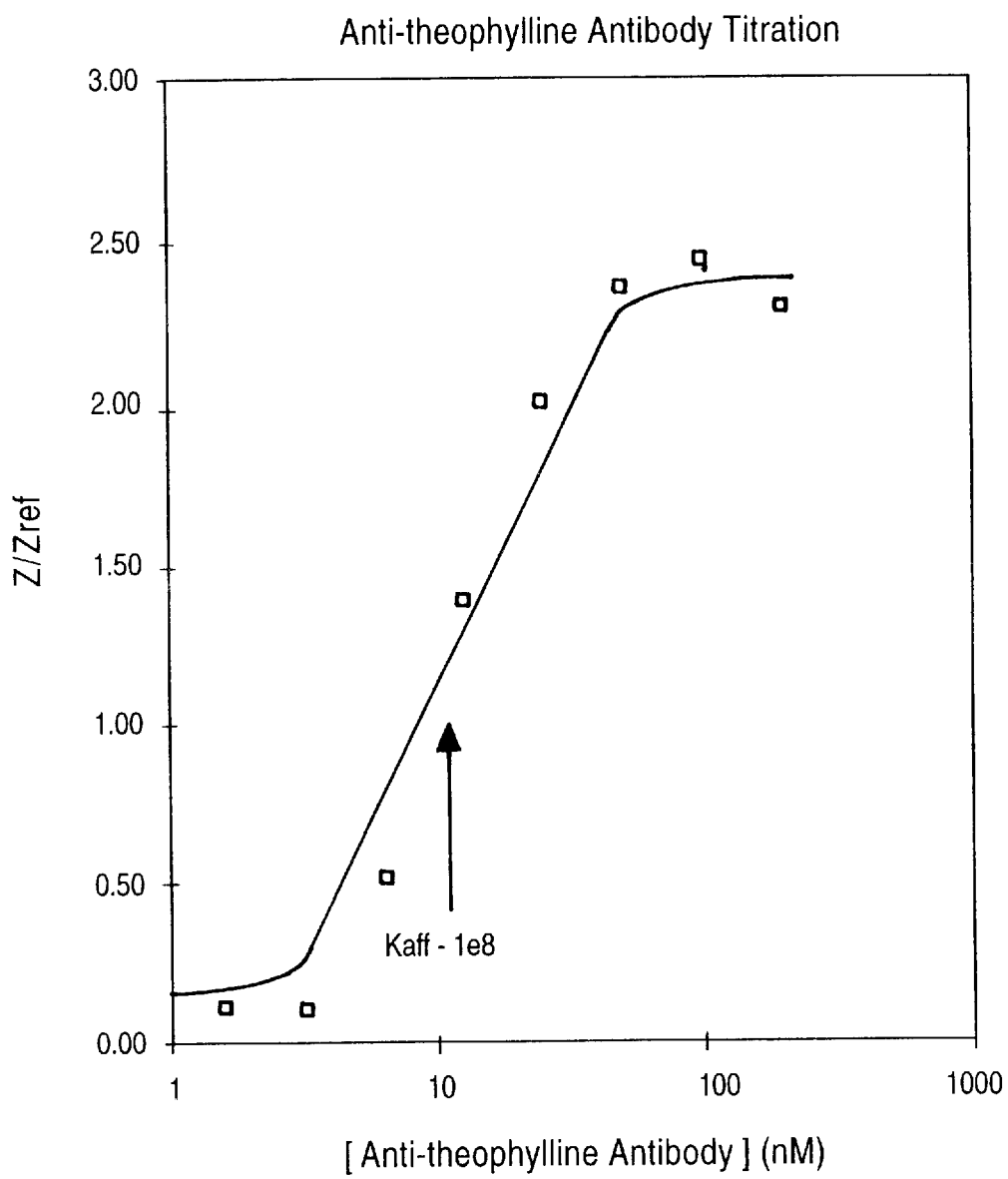
FIG. 17 shows anti-theophylline antibody titration.

The bathing PBS solution is removed from a well assembly prepared as described above and replaced with a solution of monoclonal antitheophylline antibody (BioDesign Catalogue No. G45152M [Clone: 8901, Lot No. 212704], 200 nM in PBS, 100 µl). The conduction of the membrane is observed to be rapidly reduced as a consequence of the antibody addition. The membrane response is selective to those membranes containing gramicidin-theophylline conjugate i.e. membranes constructed with gramicidin derivatives bearing ligands other than theophylline (e.g. biotin) show no response to antitheophylline antibody addition. Further more, the magnitude of the response of the gramicidin-theophylline conjugate containing membranes to treatment with antitheophylline antibody is dependent on the antibody concentration and generates a normal titration curve with 50% response at the $K_D$ of the antitheophylline-theophylline complex (FIG. 17, the ordinate shows the ratio of the final initial membrane impedance at the frequency giving the initial minimum phase angle).

Theophylline Detection

Figure 18:
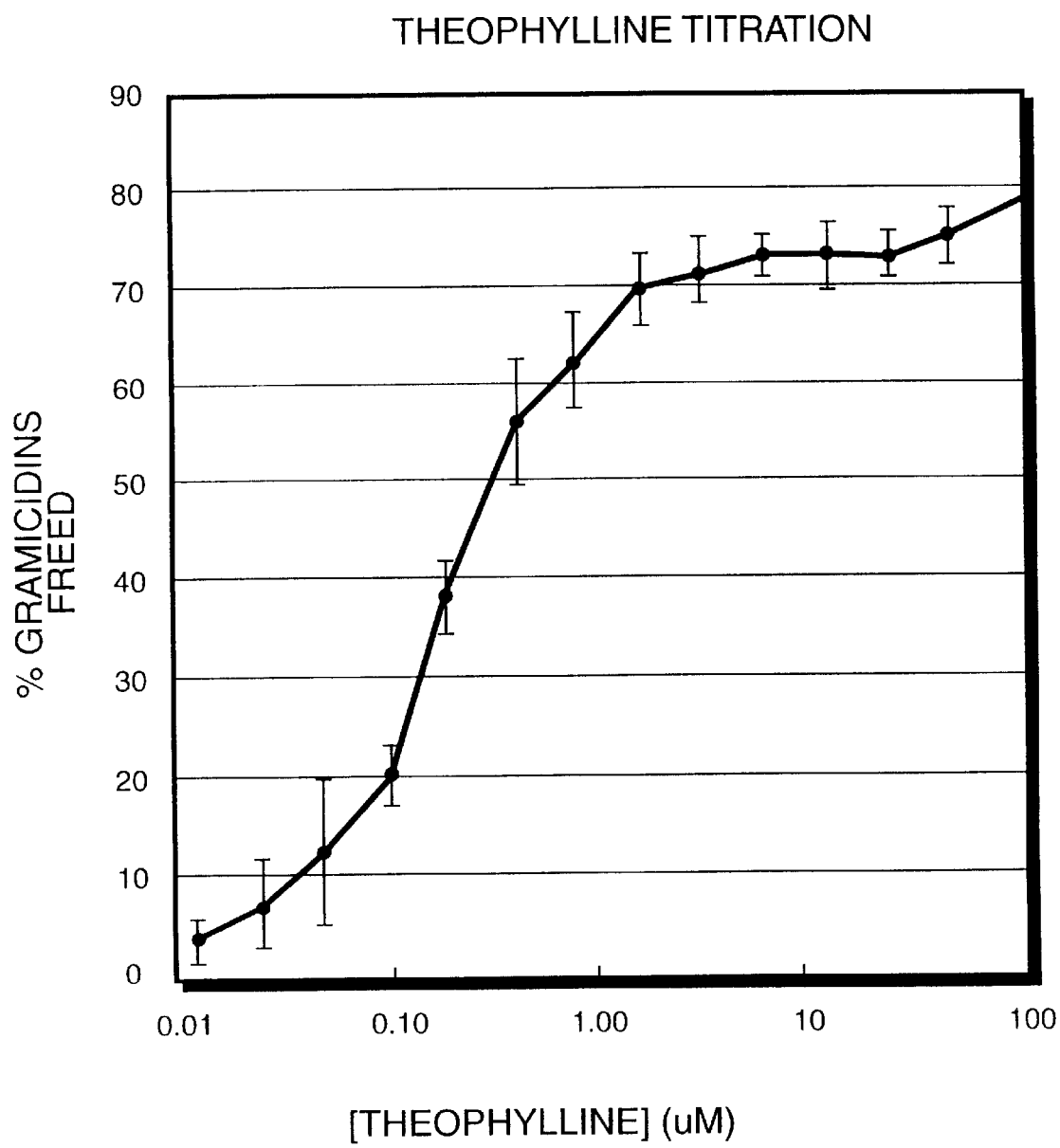
FIG. 18 shows thephylline titration.

From antitheophylline-antibody-treated wells prepared as described above is removed 50 μl of antibody solution. A solution of theophylline in PBS (50 μl, varying concentration) is added. Above a sensitivity limit of ~0.1 μM, an increase in membrane conduction is observed on exposure of the antibody treated membrane to theophylline. The magnitude of the response is related to the concentration of the theophylline solution, allowing construction of a dose-response curve (FIG. 18, the ordinate shows the proportion of those gramicidin channels initially gated off by antibody addition which are restored to conductivity by theophylline treatment). The response of the membrane to theophylline treatment is consistent with competitive displacement of antitheophylline antibody from the membrane-bound gramicidin-conjugated theophylline by free theophylline.

Synthesis

N-BOC-6-Amino Acid

To a solution of 6-aminocaproic acid (1.0 g) in 50% aqueous dioxane (12 ml) was added triethylamine (2.1 ml). The mixture was stirred at room temperature and BOC-ON (2.71 g) was added. After stirring for 1 h at 45° C., water (15 ml) and ethyl acetate (20 ml) was added to the mixture. The aqueous phase was washed with ethyl acetate (2×20 ml), acidified to pH 2 with dilute HCl and extracted with ethyl acetate. The ethyl acetate fraction was dried ($Na_2SO_4$), filtered and evaporated to dryness to yield the title compound (1.64 g).

Gramacidin N-BOC-6-Aminocaproyl Ester

To a solution of gramicidin A (500 mg), N-BOC-6-aminocaproic acid (322 mg) and 4-N,N-dimethylaminopyridine in dry, distilled dichoromethane (60 ml) under nitrogen was added to dicyclohexylcarbodiimide (164 mg). The mixture was refluxed under nitrogen for 1 h then additional N-BOC-6-aminocaproic acid (100 mg) and dicyclohexylcarbodiimide (110 mg) was added and the mixture was refluxed under nitrogen for another hour. The mixture was evaporated to dryness then thrice purified on a silica gel column (2×25 cm) eluted with dichloromethane/methanol/water (800:60:5) to afford an Ehrlich's reagent active fraction of gramicidin N-BOC-6-aminocaproyl ester (125 mg).

Gramicidin 6-Aminocaproyl Ester

Gramicidin N-BOC-6-aminocaproyl ester (204 mg) was twice layered with toluene and evaporated to dryness. The residue was dried under high vacuum then treated with trifluoroacetic acid (7.5 ml) and swirled for 3 min. The mixture was then evaporated to dryness. The residue was then layered with toluene and evaporated to dryness and dried under high vacuum. The residue was dissolved in the minimum amount of dichloromethane/ethanol (3:1), neutralised to pH 8 with triethylamine, and precipitated with water. The precipitate was centrifuges to a pellet and the supernatant was removed by decanting. The residue was dried under high vacuum to afford gramicidin 6-aminocaproyl ester (120 mg).

Gramicidin N-((7-Theophyllinyl)acetyl)-6-aminocaproyl Ester

A solution of gramicidin 6-aminocaproyl ester (20 mg), theophylline-7-acetic acid (3.6 mg) and 2-ethoxycarbonyl-1,2-dihydoquinoline (6.2 mg) in ethanol (15 ml) was stirred to 30 h. The solvent was then removed under reduced pressure and the residue was chromatographed on silica gel, eluted with dichloromethane/methanol/water/acetic acid (400:40:4:1) to afford gramicidin N-((7-Theophyllinyl) acetyl)-6-aminocaproyl ester (16 mg).

What is claimed is:

1. A membrane in which the conductance of the membrane is dependent on the presence or absence of an analyte, the membrane comprising: a first and second layer; a closely packed array of amphiphilic molecules and a plurality of gramacidin ionophores comprising a first and second half membrane spanning monomer, the first half membrane spanning monomers being provided in the first layer and the second half membrane spanning monomers being provided in the second layer, the second half membrane spanning monomers being capable of lateral diffusion within the second layer independent of the first half membrane spanning monomers, the first half membrane spanning monomers being prevented from lateral diffusion in the first layer; a first receptor molecule provided on at least the second half membrane spanning monomers; and in which a proportion of the amphiphilic molecules are membrane spanning amphiphiles which are prevented from lateral diffusion in the membrane to which are attached a second receptor molecule, the binding of an analyte to the first and second receptor molecules causing a change in the relationship between the first half membrane spanning monomers and the second half membrane spanning monomers such that the flow of ions across the membrane via the ionophores is allowed or prevented.

2. A membrane as claimed in claim 1 in which the first half membrane spanning monomers are prevented from lateral diffusion in the first layer by cross-linking the monomers and the amphiphilic molecules or by covalent attachment of the monomers to a solid surface.

3. A membrane as claimed in claim 1 in which the membrane spanning amphiphiles being archeobacterial lipids or tail to tail chemically linked bilayer amphiphiles.

4. A membrane as claimed in claim 1 in which the amphiphilic molecules are membrane spanning amphiphiles, the membrane spanning amphiphiles being archeobacterial lipids or tail to tail chemically linked bilayer amphiphiles.

5. A membrane as claimed in claim 1 in which the half membrane spanning monomers are gramicidin A monomers.

6. A membrane as claimed in claim 1 in which the first half membrane spanning monomers and the amphiphilic molecules in the first layer each include or are decorated with at least one moiety cross-linked with at least one corresponding moiety on another of these molecules.

7. A membrane as claimed in claim 1 in which the first receptor molecule has two receptor sites for the analyte.

8. A membrane as claimed in claim 1 in which the first and second receptor molecules are the same or different and are selected from the group consisting of polyclonal or monoclonal antibodies, antibody fragments, enzymes antigens, lectins, haptens, chelating agents and dyes.

9. A membrane as claimed in claim 8 in which the first and second receptor molecules are antibodies or antibody fragments.

10. A membrane as claimed in claim 1 in which the membrane is attached to a solid surface.

11. A membrane as claimed in claim 1 in which the second layer has a phase transition temperature such that cooling of the membrane below this temperature induces phase separation in the second layer thereby releasing any analyte bound to the first and/or second receptor molecules.

12. A membrane as claimed in claim 1 in which the first receptor molecule is attached to the second half membrane spanning monomer via a linker group, the linker group comprising a spacer group and one or more reactive groups, the spacer group being attached to the second half membrane spanning monomer and the reactive group providing attachment to the receptor molecule.

13. A membrane as claimed in claim 12 in which the spacer group is selected from the group consisting of hydrocarbons, oligomers of ethylene glycol, and oligo peptides; and the reactive group is selected from the group consisting of N-hydrosuccinimide esters, esters for covalent coupling to amine groups on proteins, hydrazine derivatives for coupling onto oxidised sugar residues, maleiimide derivatives, biotin, streptavidin and antibodies.

14. A membrane as claimed in claim 1 in which the first and second receptor molecules bind to different sites on the analyte, such that binding of the first and second receptors to the analyte results in a change in the flow of ions across the membrane.

15. A membrane as claimed in claim 1 in which the first and second receptor molecules are bound to different sites on the analyte or an analog thereof, the addition of analyte effecting competitive binding with the first and second receptor molecules resulting in a change in the flow of ions across the membrane.

16. A membrane as claimed in claim 1 in which the first receptor molecule binds to the second receptor molecule.

17. A membrane in which the conductance of the membrane is dependent on the presence or absence of an analyte, the membrane comprising: a first and second layer; a closely packed array of amphiphilic molecules and a plurality of gramacidin ionophores comprising a first and second half membrane spanning monomer, the first half membrane spanning monomers being provided in the first layer and the second half membrane spanning monomers being provided in the second layer, the second half membrane spanning monomers being capable of lateral diffusion within the second layer independent of the first half membrane spanning monomers, the first layer being in crystalline phase such that the first half membrane spanning monomers are prevented from lateral diffusion in the first layer; and a first receptor molecule provided on at least the second half membrane spanning monomers, said first receptor molecule binding with the analyte or a portion thereof, the binding of the analyte to the first receptor molecule causing a change in the relationship between the first half membrane spanning monomers and the second half membrane spanning monomers such that the flow of ions across the membrane via the ionophores is allowed or prevented.

18. A membrane as claimed in claim 17 in which a proportion of the amphiphlic molecules are membrane spanning amphiphiles, the membrane spanning amphiphiles being archeobacterial lipids or tail to tail chemically linked bilayer amphiphiles.

19. A membrane as claimed in claim 17 in which the amphiphilic molecules are membrane spanning amphiphiles, the membrane spanning amphiphiles being archeobacterial lipids or tail to tail chemically linked bilayer amphiphiles.

20. A membrane as claimed in claim 17 in which the half membrane spanning monomers are gramicidin A monomers.

21. A membrane as claimed in claim 17 in which the membrane includes a plurality of second receptor molecules having receptor sites remote from the first layer.

22. A membrane as claimed in claim 21 in which the second receptor molecules are prevented from diffusing laterally within the membrane.

23. A membrane as claimed in claim 22 in which the second receptor molecules are attached to membrane spanning amphiphiles.

24. A membrane as claimed in claim 17 in which the first receptor molecule has two receptor sites for the analyte.

25. A membrane as claimed in claim 21 in which the first and second receptor molecules are the same or different and are selected from the group consisting of polyclonal or monoclonal antibodies, antibody fragments, enzymes, antigens, lectins, haptens chelating agents and dyes.

26. A membrane as claimed in claim 25 in which the first and second receptor molecules are antibodies or antibody fragments.

27. A membrane as claimed in claim 17 in whch the membrane is attached to a solid surface.

28. A membrane as claimed in claim 21 in which the second layer has a phase transition temperature such that cooling of the membrane below this temperature induces phase separation in the second layer thereby releasing any analyte bound to the first and/or second receptor molecules.

29. A membrane as claimed in claim 17 in which the first receptor molecule is attached to the second half membrane spanning monomer via a linker group, the linker group comprising a spacer group and one or more reactive groups, the spacer group being attached to the second half membrane spanning monomer and the reactive group providing attachment to the receptor molecule.

30. A membrane as claimed in claim 29 in which the spacer group is selected from the group consisting of hydrocarbons, oligomers of ethylene glycol, and oligo peptides; and the reactive group is selected from the group consisting of N-hydrosuccinimide esters, esters for covalent coupling to amine groups on proteins, hydrazine derivatives for coupling onto oxidised sugar residues, maleiimide derivatives, biotin, streptavidin and antibodies.

31. A membrane as claimed in claim 29 in which the reactive group is biotin, biotin-streptavidin or an antibody or antibody fragment directed against the Fc portion of an antibody.

32. A membrane as claimed in claim 17 in which the first receptor molecules on separate second half membrane spanning monomers bind to different sites on the analyte, such that binding of the first receptors to the analyte results in a change of the flow of ions across the membrane.

33. A membrane as claimed in claim 17 in which the first receptor molecules on separate second half membrane spanning monomers are bound to different sites on the analyte or an analog thereof, such that the flow of ions across the membrane is prevented, the addition of analyte effecting competitive binding with the first receptor molecules resulting in the flow of ions across the membrane.

* * * * *